US010158038B1

(12) United States Patent
Do Valle et al.

(10) Patent No.: US 10,158,038 B1
(45) Date of Patent: Dec. 18, 2018

(54) FAST-GATED PHOTODETECTOR ARCHITECTURES COMPRISING DUAL VOLTAGE SOURCES WITH A SWITCH CONFIGURATION

(71) Applicant: HI LLC, Los Angeles, CA (US)

(72) Inventors: Bruno Do Valle, Brighton, MA (US); Rong Jin, Acton, MA (US); Jacob Dahle, Arlington, MA (US); Husam Katnani, Braintree, MA (US)

(73) Assignee: HI LLC, Los Angeles, CA (US)

( * ) Notice: Subject to any disclaimer, the term of this patent is extended or adjusted under 35 U.S.C. 154(b) by 0 days.

(21) Appl. No.: 16/051,462

(22) Filed: Jul. 31, 2018

Related U.S. Application Data

(60) Provisional application No. 62/687,659, filed on Jun. 20, 2018, provisional application No. 62/673,065, filed on May 17, 2018.

(51) Int. Cl.
*H01L 31/107* (2006.01)
*H04N 5/369* (2011.01)
*H01L 31/0352* (2006.01)
*H01L 31/0224* (2006.01)

(52) U.S. Cl.
CPC .... *H01L 31/107* (2013.01); *H01L 31/022408* (2013.01); *H01L 31/035272* (2013.01); *H04N 5/369* (2013.01)

(58) Field of Classification Search
CPC .......... G01J 1/02; G01J 5/08; G01J 2001/442; H01L 31/02027; H01L 31/107; H01L 31/02
USPC ...................................................... 250/214 R
See application file for complete search history.

(56) References Cited

U.S. PATENT DOCUMENTS

| | | | |
|---|---|---|---|
| 4,963,727 A | 10/1990 | Cova | |
| 6,240,309 B1 | 5/2001 | Yamashita et al. | |
| 6,384,663 B2 | 5/2002 | Cova et al. | |
| 6,541,752 B2 | 4/2003 | Zappa et al. | |
| 6,683,294 B1 | 1/2004 | Herbert et al. | |
| 7,507,596 B2 | 3/2009 | Yaung et al. | |
| 7,547,872 B2 | 6/2009 | Niclass et al. | |
| 7,705,284 B2 * | 4/2010 | Inoue | G01J 1/44 250/214 AG |

(Continued)

FOREIGN PATENT DOCUMENTS

| | | |
|---|---|---|
| WO | 2008144831 | 12/2008 |
| WO | 2013066959 | 5/2013 |

(Continued)

OTHER PUBLICATIONS

Bellis, Stephen et al.,"Photon counting imaging: the DigitalAPD," Society of Photo-Optical Instrumentation Engineers (SPIE) Conference Series, Feb. 2006, vol. 6068, pp. 111-120.

(Continued)

*Primary Examiner* — Que T Le
(74) *Attorney, Agent, or Firm* — ALG Intellectual Property, LLC

(57) ABSTRACT

An exemplary photodetector includes a SPAD and a capacitor. The capacitor is configured to be charged, while the SPAD is in a disarmed state, with a bias voltage by a voltage source. The capacitor is further configured to supply, when the SPAD is put in an armed state, the bias voltage to an output node of the SPAD such that a voltage across the SPAD is greater than a breakdown voltage of the SPAD.

30 Claims, 26 Drawing Sheets

(56) References Cited

U.S. PATENT DOCUMENTS

| | | |
|---|---|---|
| 8,026,471 B2 | 9/2011 | Itzler |
| 8,082,015 B2 | 12/2011 | Yodh et al. |
| 8,115,170 B2 | 2/2012 | Stellari et al. |
| 8,168,934 B2 | 5/2012 | Niclass et al. |
| 8,633,431 B2 | 1/2014 | Kim |
| 8,754,378 B2 | 6/2014 | Prescher et al. |
| 8,817,257 B2 | 8/2014 | Herve |
| 9,012,860 B2 | 4/2015 | Nyman et al. |
| 9,041,136 B2 | 5/2015 | Chia |
| 9,058,081 B2 | 6/2015 | Baxter |
| 9,076,707 B2 | 7/2015 | Harmon |
| 9,160,949 B2 | 10/2015 | Zhang et al. |
| 9,176,241 B2 | 11/2015 | Frach |
| 9,178,100 B2 | 11/2015 | Webster et al. |
| 9,190,552 B2 | 11/2015 | Brunel et al. |
| 9,201,138 B2 | 12/2015 | Eisele et al. |
| 9,209,320 B1 | 12/2015 | Webster |
| 9,257,523 B2 | 2/2016 | Schneider et al. |
| 9,257,589 B2 | 2/2016 | Niclass et al. |
| 9,299,732 B2 | 3/2016 | Webster et al. |
| 9,299,873 B2 | 3/2016 | Mazzillo et al. |
| 9,312,401 B2 | 4/2016 | Webster |
| 9,316,735 B2 | 4/2016 | Baxter |
| 9,331,116 B2 | 5/2016 | Webster |
| 9,368,487 B1 | 6/2016 | Su et al. |
| 9,401,448 B2 | 7/2016 | Bienfang et al. |
| 9,407,796 B2 | 8/2016 | Dinten et al. |
| 9,419,635 B2 | 8/2016 | Kumar et al. |
| 9,431,439 B2 | 8/2016 | Soga et al. |
| 9,442,201 B2 | 9/2016 | Schmand et al. |
| 9,449,377 B2 | 9/2016 | Sarkar et al. |
| 9,450,007 B1 | 9/2016 | Motta et al. |
| 9,466,631 B2 | 10/2016 | Fallica et al. |
| 9,476,979 B2 | 10/2016 | Drader et al. |
| 9,535,157 B2 | 1/2017 | Caley et al. |
| 9,574,936 B2 | 2/2017 | Heinonen |
| 9,625,580 B2 | 4/2017 | Kotelnikov et al. |
| 9,627,569 B2 | 4/2017 | Harmon |
| 9,639,063 B2 | 5/2017 | Dutton et al. |
| 9,640,704 B2 | 5/2017 | Frey et al. |
| 9,658,158 B2 | 5/2017 | Renna et al. |
| 9,659,980 B2 | 5/2017 | McGarvey et al. |
| 9,671,284 B1 | 6/2017 | Dandin |
| 9,685,576 B2 | 6/2017 | Webster |
| 9,702,758 B2 | 7/2017 | Nouri |
| 9,728,659 B2 | 8/2017 | Hirigoyen et al. |
| 9,741,879 B2 | 8/2017 | Frey et al. |
| 9,753,351 B2 | 9/2017 | Eldada |
| 9,767,246 B2 | 9/2017 | Dolinsky et al. |
| 9,768,211 B2 | 9/2017 | Harmon |
| 9,773,930 B2 | 9/2017 | Motta et al. |
| 9,812,438 B2 | 11/2017 | Schneider et al. |
| 9,831,283 B2 | 11/2017 | Shepard et al. |
| 9,851,302 B2 | 12/2017 | Mattioli Della Rocca et al. |
| 9,869,753 B2 | 1/2018 | Eldada |
| 9,881,963 B1 | 1/2018 | Chen et al. |
| 9,882,003 B1 | 1/2018 | Aharoni |
| 9,886,095 B2 | 2/2018 | Pothier |
| 9,899,544 B1 | 2/2018 | Mazzillo et al. |
| 9,899,557 B2 | 2/2018 | Muscara' et al. |
| 9,939,316 B2 | 4/2018 | Scott et al. |
| 9,939,536 B2 | 4/2018 | O'Neill et al. |
| 2013/0342835 A1 | 12/2013 | Blacksberg |
| 2014/0211194 A1 | 7/2014 | Pacala et al. |
| 2015/0192677 A1 | 7/2015 | Yu et al. |
| 2015/0293224 A1 | 10/2015 | Eldada et al. |
| 2015/0364635 A1 | 12/2015 | Bodlovic et al. |
| 2016/0049765 A1 | 2/2016 | Eldada |
| 2016/0119983 A1 | 4/2016 | Moore |
| 2016/0150963 A1 | 6/2016 | Roukes et al. |
| 2016/0161600 A1 | 6/2016 | Eldada et al. |
| 2016/0181302 A1 | 6/2016 | McGarvey et al. |
| 2016/0218236 A1 | 7/2016 | Dhulla et al. |
| 2016/0278715 A1 | 9/2016 | Yu et al. |
| 2016/0341656 A1 | 11/2016 | Liu et al. |
| 2016/0357260 A1 | 12/2016 | Raynor et al. |
| 2017/0030769 A1 | 2/2017 | Clemens et al. |
| 2017/0047372 A1 | 2/2017 | McGarvey et al. |
| 2017/0052065 A1 | 2/2017 | Sharma et al. |
| 2017/0118423 A1 | 4/2017 | Zhou et al. |
| 2017/0131143 A1 | 5/2017 | Andreou et al. |
| 2017/0139041 A1 | 5/2017 | Drader et al. |
| 2017/0141100 A1 | 5/2017 | Tseng et al. |
| 2017/0176579 A1 | 6/2017 | Niclass et al. |
| 2017/0176596 A1 | 6/2017 | Shpunt et al. |
| 2017/0179173 A1 | 6/2017 | Mandai et al. |
| 2017/0186798 A1 | 6/2017 | Yang et al. |
| 2017/0265822 A1 | 9/2017 | Du |
| 2017/0276545 A1 | 9/2017 | Henriksson |
| 2017/0299700 A1 | 10/2017 | Pacala et al. |
| 2017/0303789 A1 | 10/2017 | Tichauer et al. |
| 2017/0314989 A1 | 11/2017 | Mazzillo et al. |
| 2017/0363467 A1 | 12/2017 | Clemens et al. |
| 2018/0003821 A1 | 1/2018 | Imai |
| 2018/0027196 A1 | 1/2018 | Yang et al. |
| 2018/0039053 A1 | 2/2018 | Kremer et al. |
| 2018/0045816 A1 | 2/2018 | Jarosinski et al. |
| 2018/0062345 A1 | 3/2018 | Bills et al. |
| 2018/0069043 A1 | 3/2018 | Pan et al. |
| 2018/0081061 A1 | 3/2018 | Mandai et al. |
| 2018/0089848 A1 | 3/2018 | Yang et al. |
| 2018/0090526 A1 | 3/2018 | Mandai et al. |
| 2018/0090536 A1 | 3/2018 | Mandai et al. |
| 2018/0103528 A1 | 4/2018 | Moore |

FOREIGN PATENT DOCUMENTS

| | | |
|---|---|---|
| WO | 2015052523 | 4/2015 |
| WO | 2016166002 | 10/2016 |
| WO | 2017004663 | 1/2017 |
| WO | 2017130682 | 8/2017 |
| WO | 2017150146 | 9/2017 |
| WO | 2017203936 | 11/2017 |
| WO | 2018007829 | 1/2018 |

OTHER PUBLICATIONS

Cambie, Dario et al.,"Every photon counts: understanding and optimizing photon paths in luminescent solar concentrator-based photomicroreactors (LSC-PMs)," React. Chem. Eng., 2017, 2, 561-566.

Mora, Alberto D. et al., "Fast-Gated Single-Photon Avalanche Diode for Wide Dynamic Range Near Infrared Spectroscopy," IEEE Journale of Selected Topics in Quantum Electronics, vol. 16, No. 4, pp. 1023-1030, Jul./Aug. 2010.

* cited by examiner

FAST-GATED PHOTODETECTOR ARCHITECTURES COMPRISING DUAL VOLTAGE SOURCES WITH A SWITCH CONFIGURATION

RELATED APPLICATIONS

The present application claims priority under 35 U.S.C. § 119(e) to U.S. Provisional Patent Application No. 62/673,065, filed on May 17, 2018, and entitled "Photodetector Architecture," and to U.S. Provisional Patent Application No. 62/687,659, filed on Jun. 20, 2018, and entitled "Fast-Gated Photodetector Architectures." These applications are incorporated herein by reference in their respective entireties.

BACKGROUND INFORMATION

Detecting neural activity in the brain is useful for medical diagnostics, imaging, neuroengineering, brain-computer interfacing, and a variety of other diagnostic and consumer-related applications. For example, it may be desirable to detect neural activity in the brain of a patient to determine if a particular region of the brain has been impacted by reduced blood irrigation, a hemorrhage, or any other type of damage. As another example, it may be desirable to detect neural activity in the brain of a user and computationally decode the detected neural activity into commands that can be used to control various types of consumer electronics (e.g., by controlling a cursor on a computer screen, changing channels on a television, turning lights on, etc.).

A photodetector capable of detecting a single photon (i.e., a single particle of optical energy) is an example of a non-invasive detector that can be used to detect neural activity within the brain. For example, an array of these sensitive photodetectors can record photons that reflect off of tissue within the brain in response to application of one or more light pulses. Based on the time it takes for the photons to be detected by the photodetectors, neural activity and other attributes of the brain can be determined or inferred.

A photodetector that employs a semiconductor-based single-photon avalanche diode (SPAD) is capable of capturing individual photons with very high time-of-arrival resolution (a few tens of picoseconds). When photons are absorbed by a SPAD, their energy frees bound charge carriers (electrons and holes) that then become free-carrier pairs. In the presence of an electric field created by a reverse bias voltage applied to the diode, these free-carriers are accelerated through a region of the SPAD referred to as the multiplication region. As the free carriers travel through the multiplication region, they collide with other carriers bound in the atomic lattice of the semiconductor, thereby generating more free carriers through a process called impact ionization. These new free-carriers also become accelerated by the applied electric field and generate yet more free-carriers. This avalanche event can be detected and used to determine an arrival time of the photon.

In order to enable detection of a single photon, a SPAD is biased with a reverse bias voltage having a magnitude greater than the magnitude of its breakdown voltage, which is the bias level above which free-carrier generation can become self-sustaining and result in a runaway avalanche. This biasing of the SPAD is referred to as arming the device. When the SPAD is armed, a single free carrier pair created by the absorption of a single photon can create a runaway avalanche resulting in an easily detectable macroscopic current.

Conventional SPAD architectures gate a SPAD (i.e., arm and disarm the SPAD) by selectively biasing the SPAD with a gating signal generated by an active voltage source. Use of an active voltage source to gate a SPAD may disadvantageously introduce noise into the photodetector output, consume a relatively high amount of power, introduce supply voltage ripple within neighboring SPAD architectures, and cause other undesirable effects.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Fast-gated photodetector architectures are described herein. The photodetector architectures described herein can be used to fast gate a SPAD while minimizing dead time, afterpulsing, power consumption, and time jitter. The photodetector architectures described herein can therefore increase signal-to-noise ratio of photodetection, thereby improving spatial and temporal resolution compared to conventional photodetectors. These and other advantages of the photodetector architectures described herein will be described in more detail below.

Figure 1:
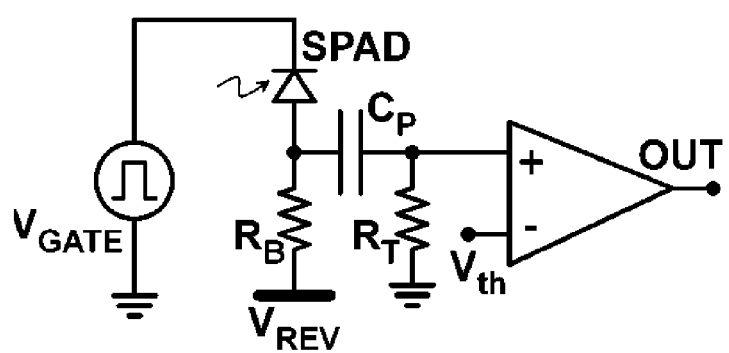
FIG. 1 shows a conventional SPAD architecture known in the art.

FIG. 1 shows a conventional SPAD architecture known in the art that may be used in a conventional photodetector. In FIG. 1, a gating signal generated by a voltage source $V_{GATE}$ is applied to an output node of a SPAD. The gating signal switches between ground and an excess bias voltage. When the gating signal is equal to ground, the voltage across the SPAD is less than or equal to a breakdown voltage of the SPAD, which means that the SPAD is in a disarmed or "off" state in which the SPAD cannot avalanche. When the gating signal is equal to the excess bias voltage, the voltage across the SPAD is greater than the breakdown voltage of the SPAD, which means that the SPAD is in an armed or "on" state in which a photon can initiate a detectable avalanche within the SPAD.

While the SPAD is in the armed state, a photon incident upon the SPAD may initiate an avalanche within the SPAD. When the avalanche occurs, current starts flowing through capacitor $C_P$ and resistors $R_B$ and $R_T$, which increases the voltage at the SPAD anode. This, in turn, reduces the voltage across the SPAD. When the voltage across the SPAD decreases below the breakdown voltage of the SPAD, the avalanche stops. This process is called passive quenching.

A number of disadvantages are associated with the conventional SPAD architecture shown in FIG. 1. For example, because the gating of the SPAD is performed directly by the voltage source $V_{GATE}$, the time it takes to arm the SPAD is not instantaneous. Rather, the time it takes to arm the SPAD depends on the rise time of the gating signal supplied by the voltage source $V_{GATE}$ (i.e., the time it takes for the gating signal to go from ground to the excess bias voltage). If a photon hits the SPAD during the rise time phase of the gating signal, the SPAD may not yet be armed and therefore may not detect the photon. Hence, any data collected by the photodetector during the rise time of the gating signal is corrupted and must be discarded.

Moreover, the passive quenching performed by the conventional SPAD architecture shown in FIG. 1 is a relatively slow process. Because the output node of the SPAD remains connected to the voltage source $V_{GATE}$ while SPAD is being passively quenched, a relatively large amount of current (and hence, power) is consumed by the SPAD architecture before the avalanche is passively quenched. A relatively slow passive quenching process may also lead to a high number of traps in the SPAD and high afterpulsing.

Another disadvantage of the conventional SPAD architecture of FIG. 1 is unwanted supply voltage ripple across a photodetector array. For example, each photodetector in an array of photodetectors may include the conventional SPAD architecture of FIG. 1. In this configuration, when an avalanche happens within a particular SPAD, a large current flow from the SPAD's voltage source (e.g., $V_{GATE}$) to the SPAD may cause voltage variations on the voltages seen by other SPADs in the photodetector array. These voltage variations are exasperated as the number of SPADs increase in a given photodetector array, and may cause variation in the SPAD parameters (e.g., probability of detecting a photon, dark current, timing, etc.).

In contrast, the SPADs in the photodetector architectures described herein are not gated directly by an active voltage source, such as voltage source $V_{GATE}$. Rather, an exemplary SPAD as described herein is gated with a capacitor that is pre-charged with a bias voltage before a command is provided to arm the SPAD. Gating the SPAD with a capacitor instead of with an active voltage source has a number of advantages and benefits.

For example, a SPAD that is gated with a capacitor may be armed practically instantaneously compared to a SPAD that is gated with an active voltage source. This is because the capacitor is already charged with the bias voltage when a command is provided to arm the SPAD. The sharper (i.e., faster) rise time provided by the photodetector architectures described herein may allow for improved depth resolution (i.e., the SPAD may be armed with greater precision, which improves the ability to time the arming of the SPAD with the time it is expected for a photon to take to reflect off a target located at a desired depth within the brain) and decreased noise (i.e., bad data that has to be discarded because it is collected before the SPAD completely transitions to the armed state).

Furthermore, a SPAD architecture that includes a SPAD that is gated with a capacitor may consume less current (and therefore power) than a conventional SPAD architecture that includes a SPAD that is gated with an active voltage source and allowed to passively quench. This is because the maximum current that the SPAD may consume during an avalanche is limited by the charge stored in the capacitor. By minimizing the power consumption of the SPAD architecture, the SPAD architectures described herein may allow for smaller power supplies to be used to power the SPAD architectures (which is particular advantageous in wearable devices). Moreover, by minimizing power consumption of a SPAD architecture, less stress is placed on the SPAD architecture over time, which may lead to increased longevity components within the SPAD architecture.

A SPAD that is gated with a capacitor also obviates the problem of supply voltage ripple that is associated with SPADs that are gated with active voltage sources. This is because the SPADs in the SPAD architectures described herein are decoupled from all active voltage sources. Hence, the SPAD architectures described herein are isolated from and do not affect performance of other SPAD architectures that are included in the same photodetector array. This isolation may result in reduced count variation and improved detection efficiency and sensitivity. These and other benefits and/or advantages that may be provided by the photodetector architectures described herein will be made apparent by the following detailed description.

Figure 2:
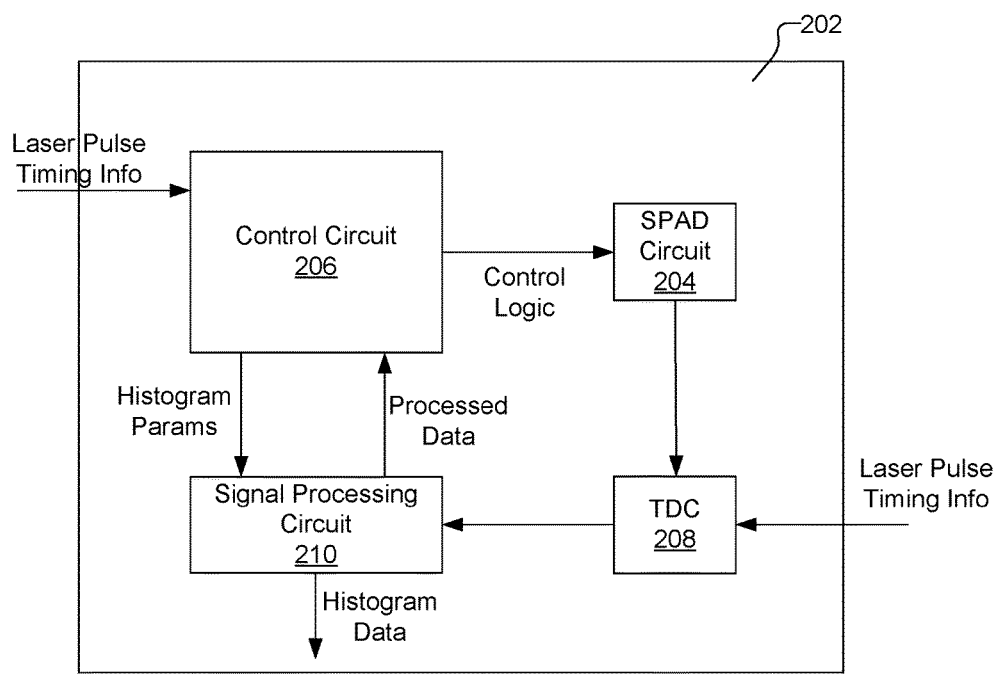
FIG. 2 illustrates various components included in an exemplary fast-gated photodetector according to principles described herein.

FIG. 2 illustrates various components included in an exemplary fast-gated photodetector 202. As shown, photodetector 202 includes a SPAD circuit 204, a control circuit 206, a time-to-digital converter (TDC) 208, and a signal processing circuit 210.

SPAD circuit 204 may include a SPAD and various other electrical components configured to operate together to detect a photon incident upon the SPAD. As will be described below, SPAD circuit 204 may generate an output pulse when SPAD circuit 204 detects a photon. Various implementations of SPAD circuit 204 will be described in detail below.

Control circuit 206 may be implemented by an application specific integrated circuit (ASIC) or any other suitable circuit configured to control an operation of various components within SPAD circuit 204. For example, as will be described in more detail below, control circuit 206 may output control logic that controls an operation of one or more switches within SPAD circuit 204 to selectively charge a capacitor within SPAD circuit 204 and put the SPAD included in the SPAD circuit 204 in either an armed or a disarmed state. In some examples, control circuit 206 may control a gate delay, which specifies a predetermined amount of time control circuit 206 is to wait after an occurrence of a light pulse (e.g., a laser pulse) to put the SPAD in the armed state. To this end, control circuit 206 may receive light pulse timing information, which indicates a time at which a light pulse occurs (e.g., a time at which the light pulse is applied to tissue within the brain). Control circuit 206 may also control a programmable gate width, which specifies how long the SPAD is kept in the armed state before being disarmed.

Control circuit 206 is further configured to control signal processing circuit 210. For example, control circuit 206 may provide histogram parameters to signal processing circuit 210. Signal processing circuit 210 may generate histogram data in accordance with the histogram parameters.

TDC 208 is configured to measure a time difference between an occurrence of an output pulse generated by SPAD circuit 204 and an occurrence of a light pulse. To this end, TDC 208 may also receive the same light pulse timing information that control circuit 206 receives. TDC 208 may be implemented by any suitable circuitry as may serve a particular implementation.

Signal processing circuit 210 is configured to perform one or more signal processing operations on data output by TDC 208. For example, signal processing circuit 210 may generate histogram data based on the data output by TDC 208 and in accordance with histogram parameters provided by control circuit 206. To illustrate, signal processing circuit 210 may generate, store, transmit, compress, analyze, decode, and/or otherwise process histograms based on the data output by TDC 208. In some examples, signal processing data 210 may provide processed data to control circuit 206, which may use the processed data in any suitable manner.

Figure 3A:
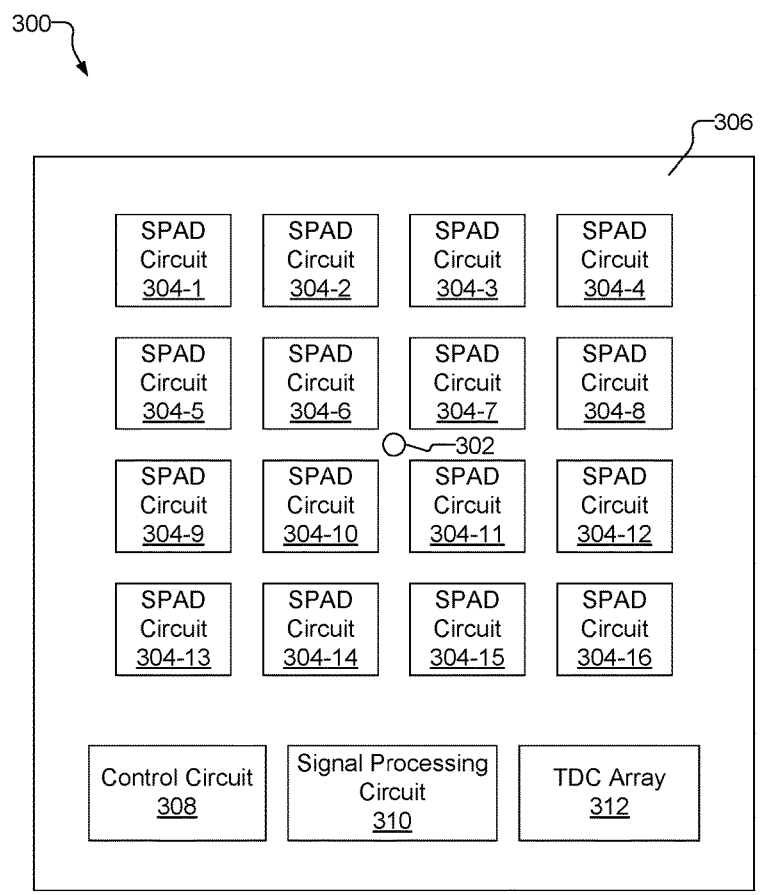
FIG. 3A illustrates an exemplary photodetector system according to principles described herein.

FIG. 3A illustrates an exemplary photodetector system 300. As shown, photodetector system 300 includes a light source 302 and a plurality of SPAD circuits 304 (i.e., SPAD circuits 304-1 through 304-16) disposed on a printed circuit board (PCB) 306. Alternatively, SPAD circuits 304 (and the other components of photodetector system 300) may be disposed on an ASIC. Photodetector system 300 further includes a control circuit 308 common to SPADs 304, a signal processing circuit 310 common to SPADs 304, and a TDC array 312 that includes a plurality of TDCs each corresponding to one of the SPAD circuits 304. Control circuit 308, signal processing circuit 310, and TDC array 312 may each be disposed on PCB 306, as shown in FIG. 3A, or located elsewhere within photodetector system 300. Each SPAD circuit 304 in combination with a TDC included in TDC array 312, control circuit 308, and signal processing circuit 304 may implement a particular photodetector. Hence, photodetector system 300 may be said to include an array of photodetectors.

Light source 302 may be configured to generate one or more light pulses at one or more wavelengths that may be applied to a desired target (e.g., a target within the brain). Light source 302 may be implemented by any suitable combination of components. For example, light source 302 may be implemented by a laser source that generates laser pulses.

SPAD circuits 304 are each similar in operation to SPAD circuit 204 and may be configured to detect photons of a light pulse generated by light source 302 after the photons reflect from a target (e.g., a target internal to a user, such as brain tissue). SPAD circuits 304 may also be used to detect photons reflected from any object due to ambient light for imaging applications. In this case, light source 302 is not needed since the photons are generated by either ambient light or another light source.

As shown, SPAD circuits 304 are arranged in a four-by-four array on PCB 306. The positioning of each SPAD circuit 304 may correspond, for example, to a pixel within a pixel array. SPAD circuits 304 may alternatively be arranged in any suitable manner. While sixteen SPAD circuits 304 are shown in FIG. 3A, it will be recognized that any number of SPAD circuits 304 may be included in photodetector system 300.

Control circuit 308 may be similar in function to control circuit 206, and may be configured to control each of SPAD circuits 308. Signal processing circuit 310 may be similar in function to signal processing circuit 210, and may be configured to process signals output by each of SPAD circuits 304. TDC array 312 may include a plurality of TDCs each similar to TDC 208 and configured to measure a time difference between the occurrence of a light pulse 302 and output pulses generated by each of SPAD circuits 304.

Photodetector system 300 may be implemented by or included in any suitable device. For example, photodetector system 300 may be included in a non-invasive wearable device that a user may wear to perform one or more diagnostic, imaging, and/or consumer-related operations.

Figure 3B:
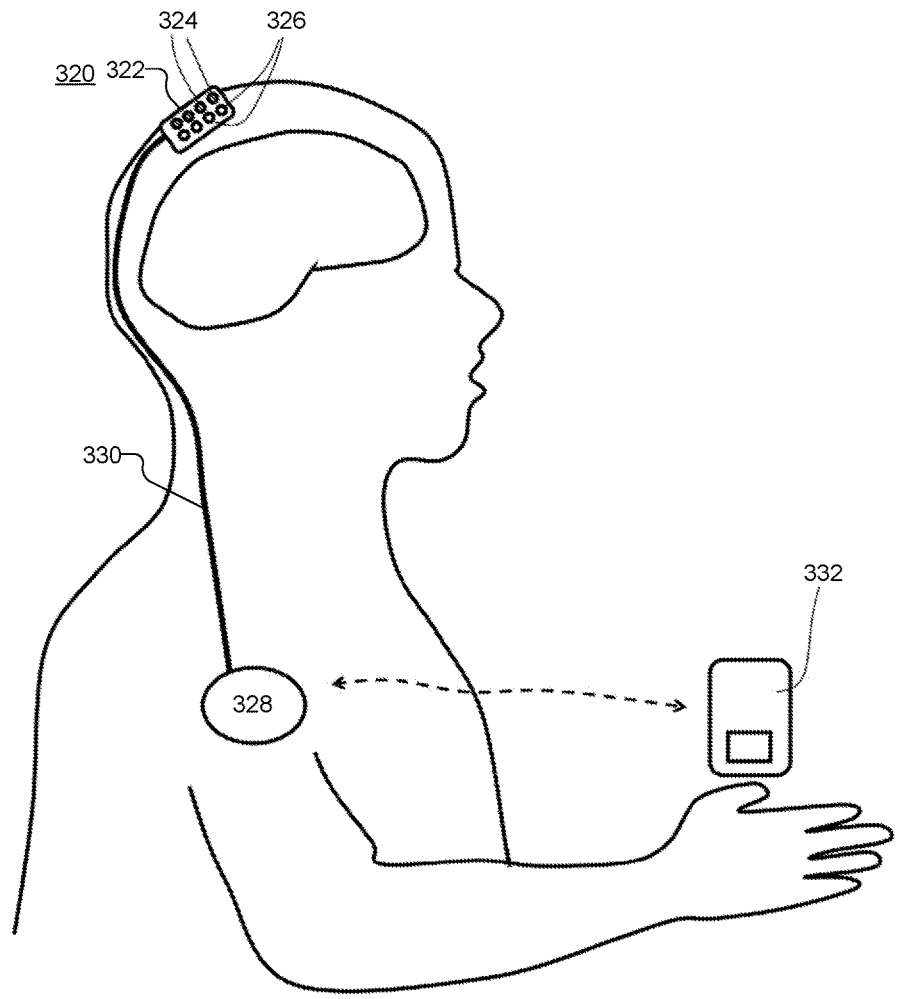
FIG. 3B shows an exemplary non-invasive wearable brain interface system that implements photodetector system according to principles described herein.

To illustrate, FIG. 3B shows an exemplary non-invasive wearable brain interface system 320 ("brain interface system 320") that implements a photodetector system, which may be similar to photodetector system 300. As shown, brain interface system 320 includes a head-mountable component 322 configured to be attached to a patient's head. Head-mountable component 322 includes a plurality of photodetectors 324 and a plurality of light sources 326 configured to generate light pulses. It will be recognized that in some alternative embodiments, head-mountable component 322 may include a single photodetector 324 and/or a single light source 326. For example, brain interface system 320 may be used for controlling an optical path and for transforming photodetector pixel measurements into an intensity value that represents an optical property of a deep brain tissue region. Brain interface system 320 allows optical detection of deep anatomical location through skin and bone by extracting data from photons originating from the deep target location, in contrast to traditional imaging systems and methods (e.g., optical coherence tomography (OCT)), which only image superficial tissue structures or through optically transparent structures.

Brain interface system 320 may further include a processor 328 configured to communicate with (e.g., control and/or receive signals from) photodetectors 324 and light sources 326 by way of a communication link 330. Communication link 330 may include any suitable wired and/or wireless communication link. Processor 328 may include any suitable housing and may be located on the patient's scalp, neck, shoulders, chest, or arm, as may be desirable. In some variations, processor 328 may be integrated in the same assembly housing as photodetectors 324 and light sources 326.

As shown, brain interface system 320 may optionally include a remote processor 332 in communication with processor 328. For example, remote processor 332 may store measured data from photodetectors 324 and/or processor 328 from previous detection sessions. Power for photodetectors 324, light sources 326, and/or processor 238 may be provided via a wearable battery (not shown). In some examples, processor 328 and the battery may be enclosed in a single housing, and wires carrying power signals from processor 328 and the battery may extend to photodetectors 324 and light sources 326. Alternatively, power may be provided wirelessly (e.g., by induction).

Photodetector system 300 may alternatively be included in a non-wearable device (e.g., a medical device and/or consumer device that is placed near the head or other body part of a user to perform one or more diagnostic, imaging, and/or consumer-related operations). Photodetector system 300 may alternatively be included in a sub-assembly enclosure of a wearable invasive device (e.g., an implantable medical device for brain recording and imaging).

Various SPAD circuits that may be used in the photodetector architectures described herein will now be described. Each of the SPAD circuits described herein are gated with a capacitor (or, in some cases, with a parasitic capacitance of the SPAD itself) that is pre-charged with a bias voltage before a command is provided to arm the SPAD.

Figure 4A:
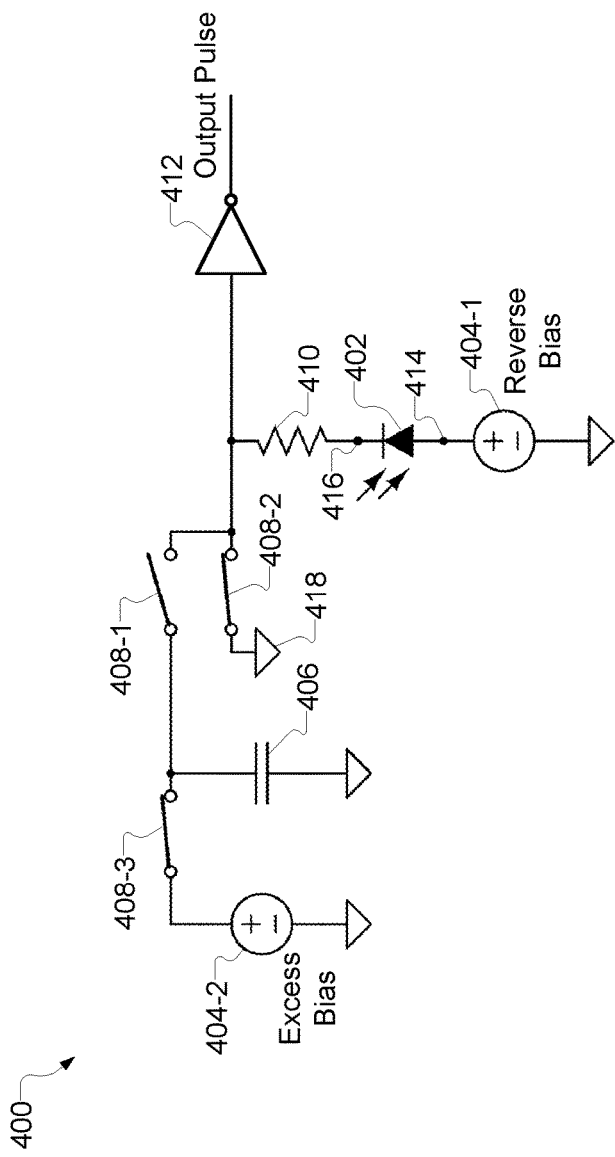
FIG. 4A shows an exemplary SPAD circuit that may be used in the photodetector architectures described herein.

FIG. 4A shows an exemplary SPAD circuit 400 that may be used in the photodetector architectures described herein. As shown, SPAD circuit 400 includes a SPAD 402, voltage sources 404-1 and 404-2, a capacitor 406, a plurality of switches 408 (i.e., switches 408-1, 408-2, and 408-3), a resistor 410, and an inverter 412.

As shown, voltage source 404-1 is connected to an input node 414 (also referred to as an anode) of SPAD 402. Voltage source 404-1 may include any suitable active voltage source configured to supply a reverse bias voltage at input node 414. The reverse bias voltage has a magnitude that is equal to or less than a breakdown voltage of SPAD 402. In some examples, the reverse bias voltage supplied by voltage source 404-1 has a magnitude that is less than the breakdown voltage of SPAD 402 by a predetermined amount. For example, the reverse bias voltage supplied by voltage source 404-1 may be within 1-2 volts of the breakdown voltage of SPAD 402. An exemplary breakdown voltage of SPAD 402 is 20 volts. Hence, an exemplary, but not exclusive, magnitude of the reverse bias voltage supplied by voltage source 404-1 is 18-19 volts.

Voltage source 404-2 may include any suitable active voltage source and is configured to be selectively connected to capacitor 406 by way of switch 408-3. For example, voltage source 404-2 is connected to capacitor 406 when switch 408-3 is closed and disconnected from capacitor 406 when switch 408-3 is open. When voltage source 404-2 is connected to capacitor 406, voltage source 404-2 charges capacitor 406 with an excess bias voltage. In some examples, the excess bias voltage has a magnitude that is less than or equal to the breakdown voltage of SPAD 402 (e.g., less than the magnitude of the reverse bias voltage supplied by voltage source 404-1). For example, the excess bias voltage may be 2-5 volts. However, the excess bias voltage may have any other suitable value as may serve a particular implementation.

In some examples, the excess bias voltage may be set to a value that compensates for the parasitic capacitance of SPAD 402. It will be recognized that when capacitor 406 is connected to SPAD 402, some of the charge on capacitor 406 will be transferred to the parasitic capacitance of SPAD 402. Hence, the excess bias voltage may be set to ensure that the total voltage across SPAD 402 exceeds the breakdown voltage of SPAD 402 even after the parasitic capacitance of SPAD 402 is charged.

Switches 408 (also referred to herein as a "switch configuration") are configured to selectively arm and disarm SPAD 402. For example, as will be illustrated below, switches 408-1 and 408-2 may put SPAD 402 into an armed state by connecting capacitor 406 to an output node 416 (also referred to as a cathode) of SPAD 402 while capacitor 406 is charged with the excess bias voltage and while capacitor 406 is disconnected from voltage source 404-2. As shown, capacitor 406 may be connected to output node 416 by way of resistor 410. In some alternative embodiments, resistor 410 is connected between SPAD 402 and voltage source 404-1. In yet other alternative embodiments, resistor 410 is not included in SPAD circuit 400, and capacitor 406 may be connected directly to output node 416.

When capacitor 406 is connected to output node 416, capacitor 406 supplies the excess bias voltage to output node 416. This causes the voltage across SPAD 402 to be greater than the breakdown voltage of SPAD 402, thereby putting SPAD 402 in the armed state. For example, if the breakdown voltage of SPAD 402 is 20 volts, the reverse bias voltage as supplied by voltage source 404-1 at input node 414 is −18 volts, and the excess bias voltage supplied by capacitor 406 at output node 416 is 3 volts when capacitor 406 is fully charged, the voltage across SPAD 402 is 21 volts when capacitor 406, which is greater than the breakdown voltage of SPAD 402.

Capacitor 406 may be of any suitable size (i.e., capacity). In some examples, the size of capacitor 406 may be relatively small in order to reduce the current flow through SPAD 402 during an avalanche. This minimizes power consumption, quench time, afterpulsing, and time jitter.

Switches 408-1 and 408-2 may put SPAD 402 into a disarmed state by disconnecting capacitor 406 from output node 416 of SPAD 402 and connecting the output node of SPAD 402 to ground 418. In this configuration, the voltage across SPAD 402 is substantially equal to the magnitude of the reverse bias voltage, which is less than the breakdown voltage of SPAD 402.

Inverter 412 is configured to generate an output pulse when a photon hits SPAD 402 while SPAD 402 is in the armed state. When a photon initiates an avalanche within SPAD 402, SPAD 402 draws current from capacitor 406, which discharges capacitor 406 to zero. As capacitor 406 is discharged, the voltage at output node 416 decreases. When the voltage at output node 416 drops below a certain value, inverter 412 generates an output pulse. In some examples, a power supply to inverter 412 is adjustable to account for different thresholds.

Figure 4B:
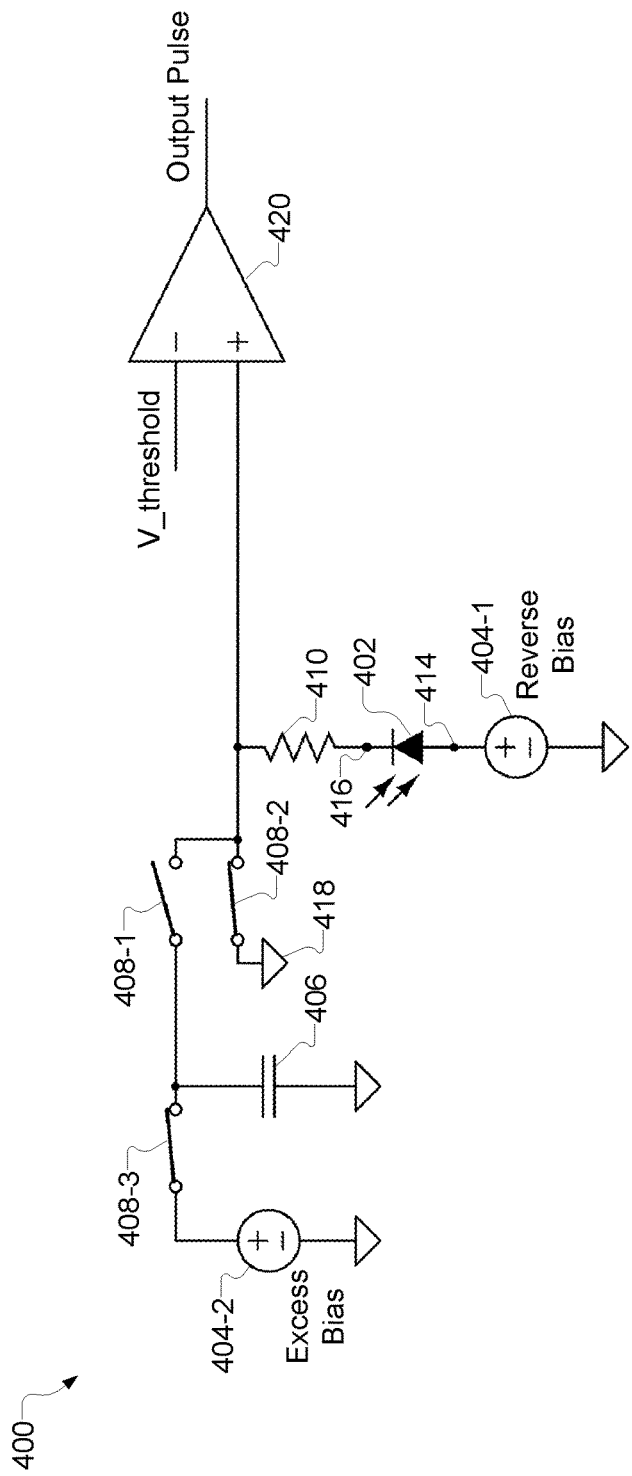
FIG. 4B shows another exemplary SPAD circuit that may be used in the photodetector architectures described herein.

FIG. 4B shows an alternative implementation of SPAD circuit 400 in which a comparator 420 is included in SPAD circuit 400 in place of inverter 412. Comparator 420 is configured to generate an output pulse when a photon hits SPAD 402 while SPAD 402 is in the armed state. To this end, comparator 420 has a negative terminal and a positive terminal. A threshold voltage (V_threshold) is on the negative terminal. This threshold voltage is less than voltage across SPAD 402 while SPAD 402 is in the armed state and capacitor 406 is fully charged with the excess bias voltage. The positive terminal of comparator 420 is connected to output node 416 (e.g., by way of resistor 410). When a photon initiates an avalanche within SPAD 402, SPAD 402 draws current from capacitor 406, which discharges capacitor 406 to zero. As capacitor 406 is discharged, the voltage at output node 416 decreases. When the voltage at output node 416 drops below the threshold voltage on the negative terminal of comparator 420, comparator 420 generates an output pulse.

Figure 5:
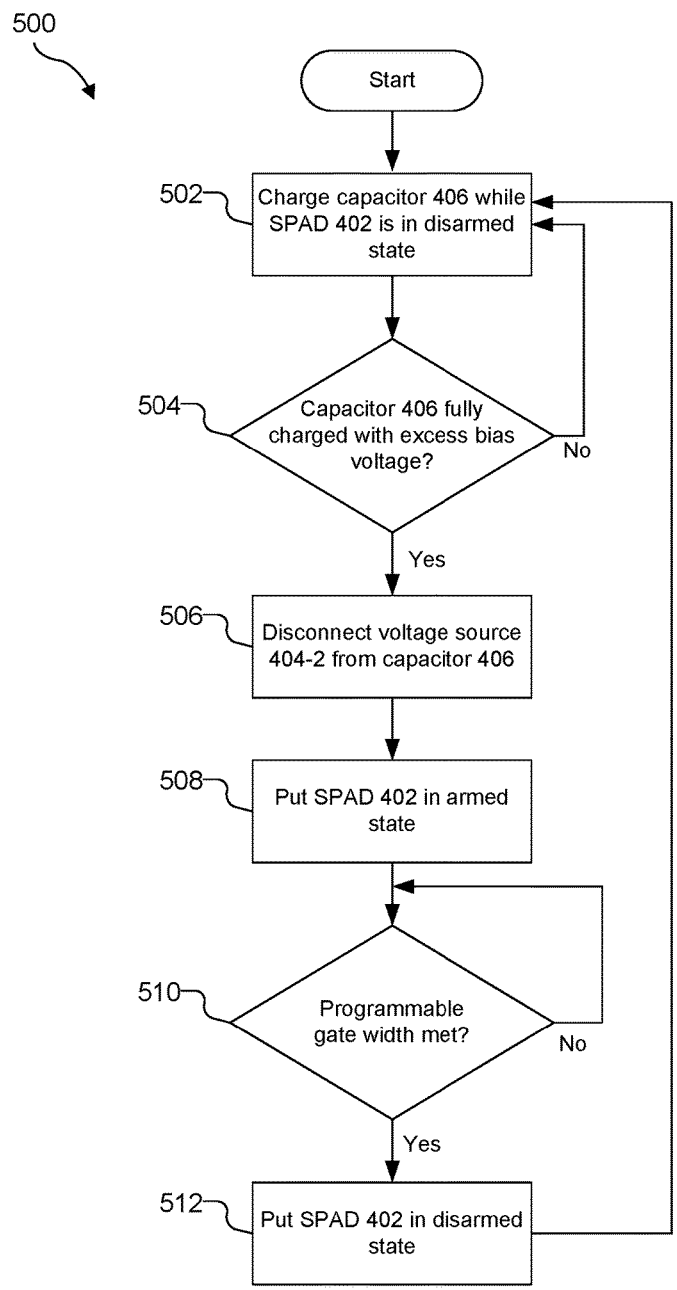
FIG. 5 is a flowchart that illustrates an exemplary mode of operation of the SPAD circuit of FIG. 4A according to principles described herein.

FIG. 5 is a flowchart 500 that illustrates an exemplary mode of operation of SPAD circuit 400. For purposes of this example, control circuit 206 is configured to control SPAD circuit 400 by controlling switches 408, TDC 208 is connected to the output of inverter 412, and signal processing circuit 210 is connected to the output of TDC 208. One or more of the operations shown in flowchart 500 may be performed by control circuit 206.

In operation 502, capacitor 406 is charged with the excess bias voltage while SPAD 402 is in a disarmed state. Control circuit 206 may cause capacitor 406 to be charged with the excess bias voltage while SPAD 402 is in the disarmed state by providing control logic that opens switch 408-1 to disconnect output node 416 of SPAD 402 from capacitor 406, closes switch 408-2 to connect output node 416 of SPAD 402 to ground 418, and closes switch 408-3 to connect voltage source 404-2 to capacitor 406. This switch state is shown in FIG. 4A.

Figure 6:
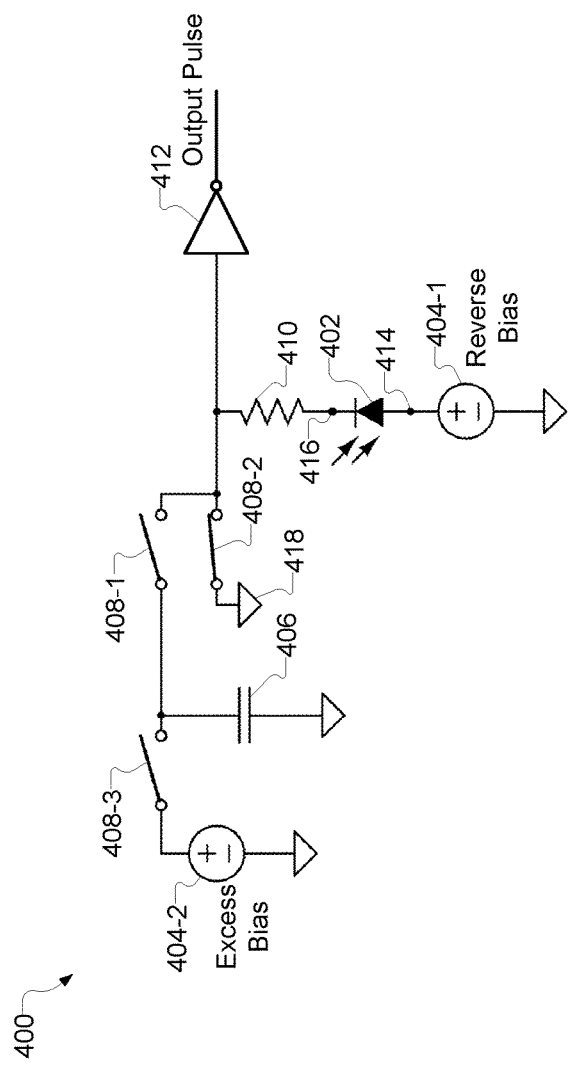
FIGS. 6-7 show exemplary switch states of the SPAD circuit of FIG. 4A.

While in the switch state shown in FIG. 4A, voltage source 404-2 charges capacitor 406 with the excess bias voltage. When control circuit 206 detects that capacitor 406 is fully charged with the excess bias voltage (Yes; decision block 504), control circuit 506 disconnects voltage source 404-2 from capacitor 406 (operation 506). This is performed by control circuit 506 providing control logic that opens switch 408-3 while switch 408-1 is still open and switch 408-2 is still closed. This switch state is shown in FIG. 6.

Figure 7:
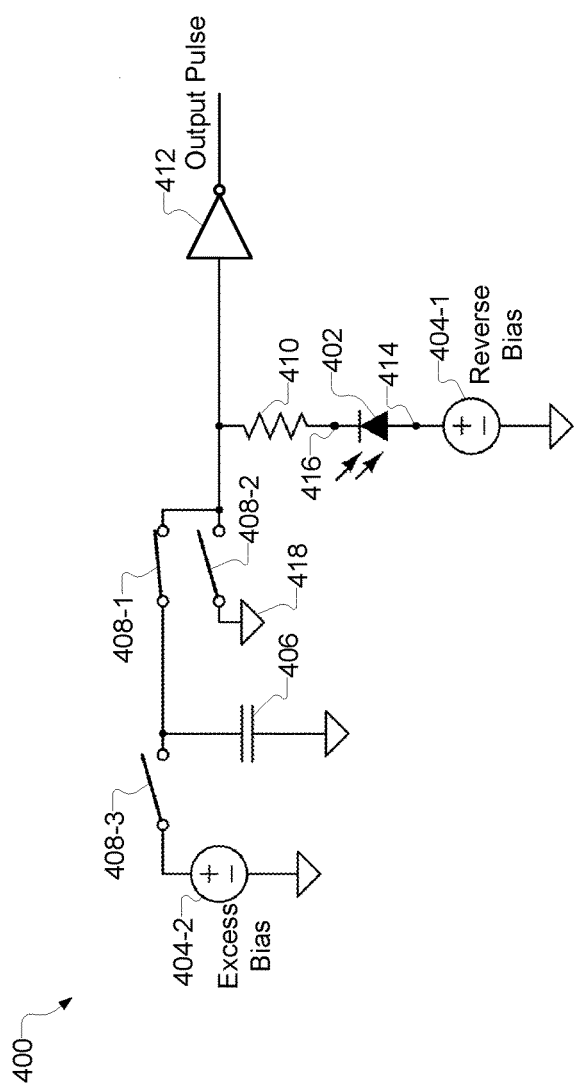

In operation 508, control circuit 206 puts SPAD 402 in an armed state once capacitor 406 is charged with the excess bias voltage. To this end, control circuit 206 provides control logic that closes switch 408-1 to connect output node 416 of SPAD 402 to capacitor 406, opens switch 408-2 to disconnect output node 416 of SPAD 402 from ground 418, and keeps switch 408-3 open to keep the voltage source 404-2 disconnected from capacitor 406. This switch state is shown in FIG. 7. While in the switch state shown in FIG. 7, SPAD 402 is armed because the voltage across SPAD 402 is higher than the breakdown voltage of SPAD 402.

In some examples, control circuit 206 waits to put SPAD 402 in the armed state until a predetermined amount of time elapses after an occurrence of a light pulse (e.g., a light pulse generated by light source 302). In this manner, SPAD circuit 402 may be configured to detect a photon arriving from a particular depth within a user (e.g., a particular depth within the brain of the user).

For example, control circuit 206 may maintain data representative of a programmable gate delay. The programmable gate delay specifies a predetermined amount of time that control circuit 206 is to wait after an occurrence of a light pulse to put SPAD 402 in the armed state. The programmable gate delay may be programmed by a user (e.g., via a software and/or hardware interface with control circuit 206) to specify any suitable amount of time. Additionally or alternatively, the programmable gate delay may be determined by signal processing circuit 210.

Control circuit 206 may use the programmable gate delay by detecting an occurrence of a light pulse (e.g., by receiving light pulse timing information that specifies a time that the light pulse is generated) while SPAD 402 is in the disarmed state and putting SPAD 402 in the armed state a predetermined amount of time, as specified by the programmable gate delay, after the occurrence of the light pulse. Control circuit 206 may alternatively set SPAD 402 to always be armed by closing switches 408-1 and 408-3 while keeping switch 408-2 open.

Figure 8:
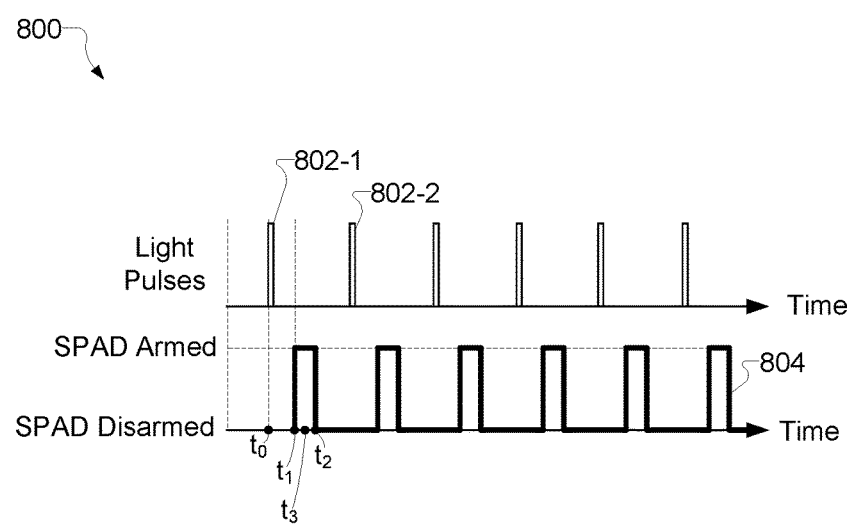
FIG. 8 shows an exemplary timing diagram that illustrates a relationship between the occurrence of a light pulse and a programmable gate delay according to principles described herein.

FIG. 8 shows an exemplary timing diagram 800 that illustrates a relationship between the occurrence of a light pulse and the programmable gate delay used by control circuit 206. As shown, a sequence of light pulses 802 (e.g., light pulses 802-1 and 802-2) may be applied to a target (e.g., tissue within the brain of a user). An exemplary frequency at which light pulses 802 are applied is 40-100 megahertz.

During the application of the sequence of light pulses 802, SPAD 402 is armed and disarmed in accordance with one or more timing parameters (e.g., a programmable gate delay, a programmable gate width, etc.) maintained by control circuit 406. This arming and disarming is represented by pulse wave 804. As shown, when pulse wave 804 is high, SPAD 402 is in the armed state. When pulse wave 804 is low, SPAD 402 is in the disarmed state.

As shown, each light pulse 802 occurs (i.e., is applied) while SPAD 402 is in the disarmed state. Each light pulse 802 occurs at a particular time. For example, light pulse 802-1 occurs at time $t_0$. The programmable gate delay maintained by control circuit 206 specifies how long control circuit 206 waits until outputting control data that puts SPAD 402 in the armed state. In the example of FIG. 8, SPAD 402 is put into the armed state at time $t_1$. Hence, the programmable gate delay is equal to $t_1-t_0$. An exemplary programmable gate delay is between zero picoseconds and 4 nanoseconds. As mentioned above, the rise time associated with SPAD 402 going from the disarmed state to the armed state is relatively fast (e.g., almost instantaneous) because SPAD 402 is being gated by capacitor 406 instead of by an active voltage source.

In some examples, control circuit 206 also maintains data representative of a programmable gate width, which specifies how long SPAD 402 is kept in the armed state before being disarmed. The programmable gate width may be programmed by a user (e.g., via a software and/or hardware interface with control circuit 206) to specify any suitable amount of time. Additionally or alternatively, the programmable gate width may be derived in signal processing circuit 210.

In the timing diagram of FIG. 8, SPAD 402 is disarmed at time $t_2$. Hence, the programmable gate width in this example is equal to $t_2-t_1$. By controlling the gate width, control circuit 206 may ensure that SPAD 402 is disarmed for a relatively long time before the occurrence of a subsequent light pulse. This may advantageously avoid afterpulsing, which may distort data acquired by the photodetector by triggering an output pulse by inverter 412 that is not indicative of an arrival of an actual photon.

Accordingly, if control circuit 206 detects that the programmable gate width is met (i.e., that the predetermined time specified by the programmable gate width has expired) (Yes; decision block 510), control circuit 206 puts SPAD 402 back in the disarmed state (operation 512) by opening switch 408-1 to disconnect output node 416 of SPAD 402 from capacitor 406 and closing switch 408-2 to connect output node 416 of SPAD 402 to ground 418. The process shown in FIG. 5 may be repeated for subsequent light pulses. For example, while SPAD 402 is in the disarmed state, capacitor 406 may again be charged so that SPAD 402 may again be armed and detect a photon from light pulse 802-2.

Once SPAD 402 has been put in the armed state, a photon from the light pulse may initiate an avalanche within SPAD 402. As described above, SPAD 402 draws current from capacitor 406 while the avalanche is occurring, which decreases the voltage at output node 416. When the voltage at output node 416 drops below a certain value, inverter 412 generates an output pulse.

TDC 208 may measure a time difference between an occurrence of the output pulse generated by inverter 412 and an occurrence of light pulse 802-1 in any suitable manner. For example, referring to FIG. 8, inverter 412 may generate an output pulse at time $t_3$. TDC 208 may measure a time difference between the occurrence of the output pulse and the occurrence of light pulse 802-1 by computing a difference between $t_3$ and $t_0$. Alternatively, TDC 208 may compute a difference between $t_3$ and an occurrence of a subsequent light pulse (i.e., light pulse 802-2) and thereby determine the time difference between the occurrence of the output pulse and the occurrence of light pulse 802-1.

TDC 208 may output data representative of the time difference between the occurrence of the output pulse and the occurrence of light pulse 802-1 to signal processing circuit 210. Signal processing circuit 210 may perform one or more of the signal processing operations described herein on the data.

Figure 9A:
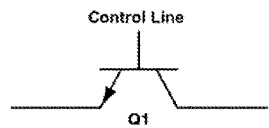
FIGS. 9A-9F show various circuits that may implement any of the switches described herein.
Figure 9B:
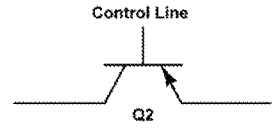
Figure 9C:
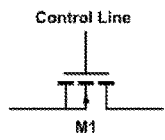
Figure 9D:
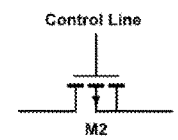
Figure 9E:
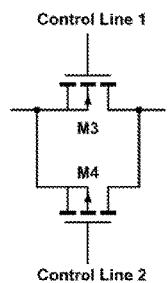
Figure 9F:
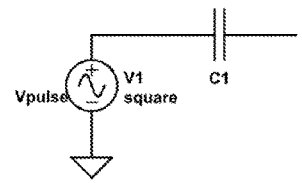

The various components included in SPAD circuit 400 may be implemented in any suitable manner. For example, switches 408 may each be implemented by any suitable switch circuitry. To illustrate, FIGS. 9A-9F show various circuits that may implement any of switches 408. In particular, FIG. 9A shows an NPN bipolar junction transistor that may implement one or more of switches 408, FIG. 9B shows PNP bipolar junction transistor that may implement one or more of switches 408, FIG. 9C shows an NMOS MOSFET that may implement one or more of switches 408, FIG. 9D shows a PMOS MOSFET that may implement one or more of switches 408, FIG. 9E shows a transmission gate that may implement one or more of switches 408, and FIG. 9F shows a square wave generator and a capacitor that may implement one or more of switches 408.

Figure 10A:
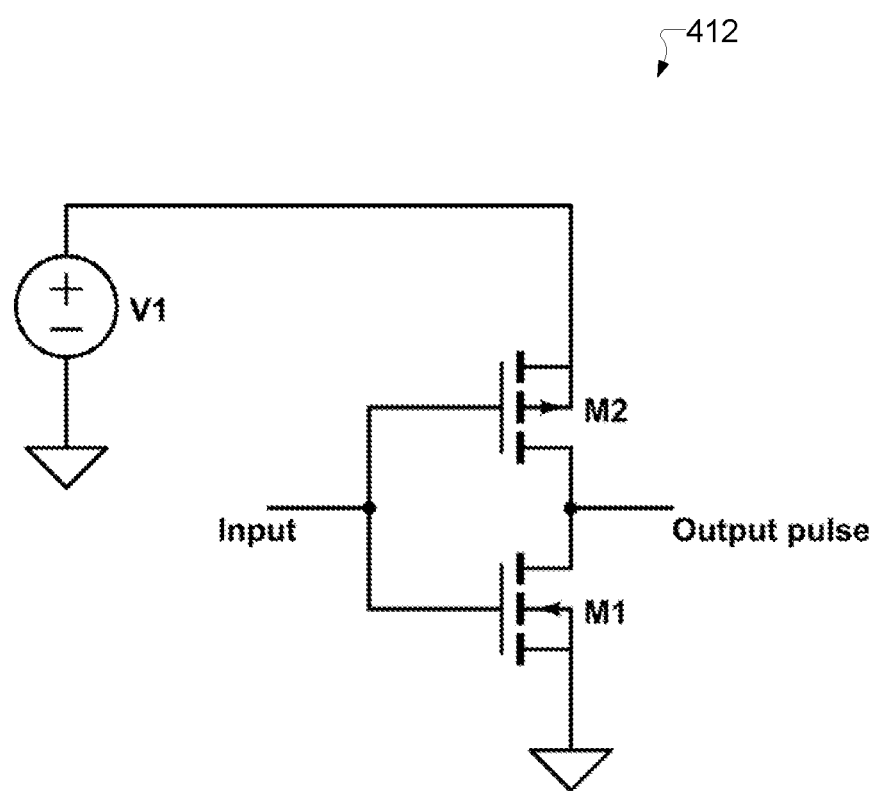
FIG. 10A illustrates an exemplary implementation of an inverter according to principles described herein.

FIG. 10A illustrates an exemplary implementation of inverter 412. In this implementation, when an avalanche happens, the voltage on output node 416 of SPAD 402 drops close to zero, causing the output pulse generated by inverter 412 to go high. Various other circuit topologies may implement inverter 412 as may serve a particular implementation.

Figure 10B:
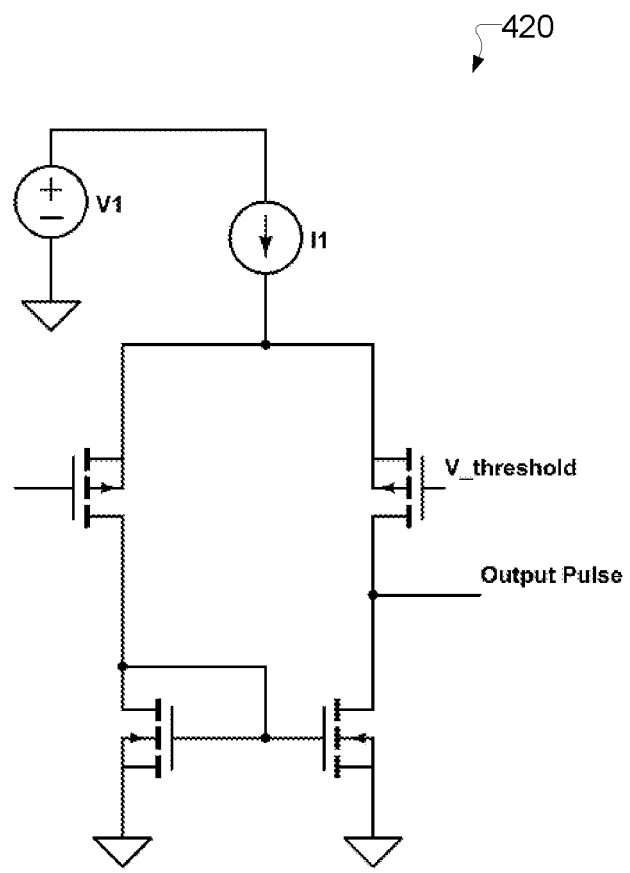
FIG. 10B illustrates an exemplary implementation of a comparator according to principles described herein.

FIG. 10B illustrates an exemplary implementation of comparator 420. In this implementation, when an avalanche happens, the voltage on output node 416 of SPAD 402 drops close to zero, causing the output pulse generated by comparator 420 to go high. Various other circuit topologies may implement comparator 420 as may serve a particular implementation.

In some examples, inverter 412 and comparator 420 may be omitted from SPAD circuit 400. In these examples, the output from SPAD 402 is provided as the input to TDC 208.

Figure 11A:
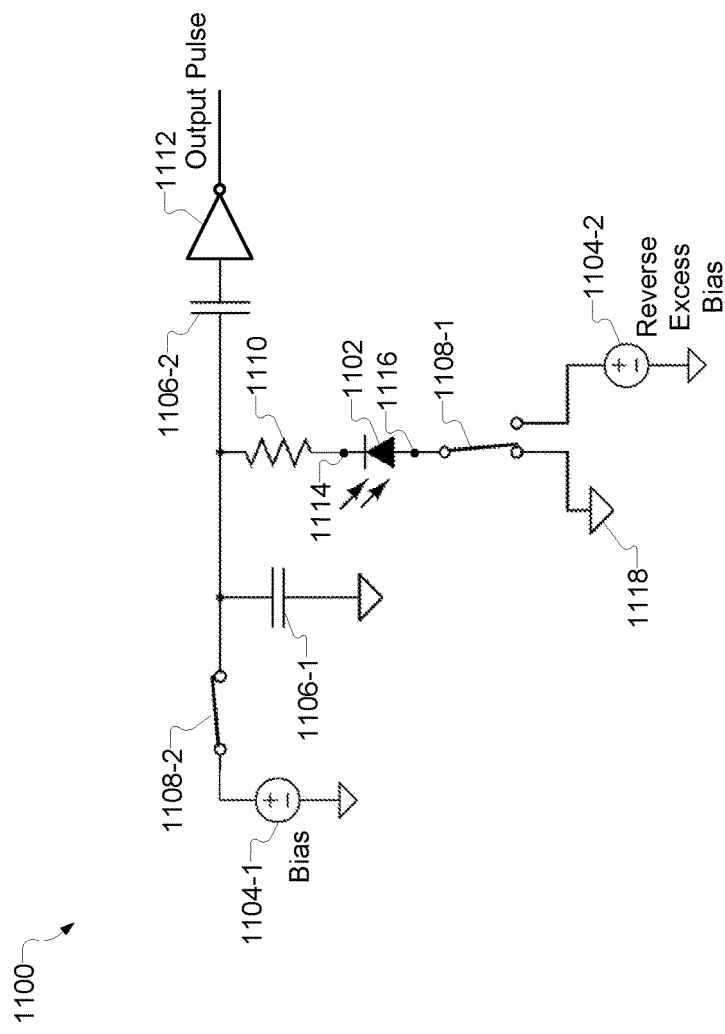
FIG. 11A shows another exemplary SPAD circuit that may be used in the photodetector architectures described herein.

FIG. 11A shows another exemplary SPAD circuit 1100 that may be used in the photodetector architectures described herein. As shown, SPAD circuit 1100 includes a SPAD 1102, voltage sources 1104-1 and 1104-2, capacitors 1106-1 and 1106-2, a plurality of switches 1108 (i.e., switches 1108-1 and 1108-2), a resistor 1110, and an inverter 1112.

As shown, capacitor 1106-1 is connected to an output node 1114 of SPAD 1102. Capacitor 1106-1 may have any suitable size as may serve a particular implementation. Capacitor 1106-1 is shown to be connected to output node 1114 by way of resistor 1110. In some examples, resistor 1110 is not actually a physical resistor, but represents the internal resistance of SPAD 1102.

Voltage source 1104-1 may include any suitable active voltage source and is configured to be selectively connected to capacitor 1106-1 by way of switch 1108-2. For example, voltage source 1104-1 is connected to capacitor 1106-1 when switch 1108-1 is in a first position and disconnected from capacitor 1106-1 when switch 1108-1 is in a second position. In the examples provided herein, switch 1108-1 is closed while in the first position and open while in the second position. It will be recognized that in alternative configurations, voltage source 1104-1 may be connected to capacitor 1106-1 when switch 1108-1 is open and disconnected from capacitor 1106-1 when switch 1108-1 is closed.

When voltage source 1104-1 is connected to capacitor 1106-1, voltage source 1104-1 charges capacitor 1106-1 with a bias voltage. The bias voltage has a magnitude that equal to or less than a breakdown voltage of SPAD 1102. In some examples, the bias voltage supplied by voltage source 1104-1 has a magnitude that is less than the breakdown voltage of SPAD 1102 by a predetermined amount. For example, the bias voltage supplied by voltage source 1104-1 may be within 1-2 volts of the breakdown voltage of SPAD 1102. An exemplary breakdown voltage of SPAD 1102 is 20 volts. Hence, an exemplary, but not exclusive, magnitude of the bias voltage supplied by voltage source 1104-1 is 18-19 volts.

As shown, voltage source 1104-2 is connected to an input node 1116 of SPAD 1102. Voltage source 1104-2 may include any suitable active voltage source configured to supply a reverse excess bias voltage at input node 1116. In some examples, the reverse excess bias voltage has a magnitude that is less than or equal to the breakdown voltage of SPAD 1102 (e.g., less than or equal to the magnitude of the bias voltage supplied by voltage source 1104-1). For example, the reverse excess bias voltage may be negative 2-5 volts. However, the reverse excess bias voltage may have any other suitable value as may serve a particular implementation. As described above, the reverse excess bias voltage may be set to a value that compensates for the parasitic capacitance of SPAD 1102.

Switches 1108 are configured to selectively arm and disarm SPAD 1102. For example, as will be illustrated below, switch 1108-1 may put SPAD 1102 into an armed state by connecting voltage source 1104-2 to input node 1116 of SPAD 1102 while capacitor 1106-1 is both charged with the bias voltage and disconnected from voltage source 1104-1.

When voltage source 1104-2 is connected to input node 1116, voltage source 1104-2 supplies the reverse excess bias voltage to input node 1116. This causes the voltage across SPAD 1102 to be greater than the breakdown voltage of SPAD 1102, thereby putting SPAD 1102 in the armed state. For example, if the breakdown voltage of SPAD 1102 is 20 volts, the bias voltage as supplied by capacitor 1106-1 at output node 1114 is 18 volts when capacitor 1106-1 is fully charged, and the reverse excess bias voltage supplied by voltage source 1104-2 at input node 1116 is −3 volts, the voltage across SPAD 1102 is 21 volts, which is greater than the breakdown voltage of SPAD 1102.

Switch 1108-1 may put SPAD 1102 into a disarmed state by disconnecting voltage source 1104-2 from input node 1116 of SPAD 1102 and connecting input node 116 of SPAD 1102 to ground 1118. In this configuration, the voltage across SPAD 1102 is substantially equal to the magnitude of the bias voltage, which is less than the breakdown voltage of SPAD 1102.

Inverter 1112 is similar to inverter 412 and is configured to generate an output pulse when a photon hits SPAD 1102 while SPAD 1102 is in the armed state. When a photon initiates an avalanche within SPAD 1102, SPAD 1102 draws current from capacitor 1106-1, which discharges capacitor 1106-1 to zero. As capacitor 1106-1 is discharged, the voltage at output node 1114 decreases. When the voltage at output node 1114 drops below a certain value, inverter 1112 generates an output pulse.

Figure 11B:
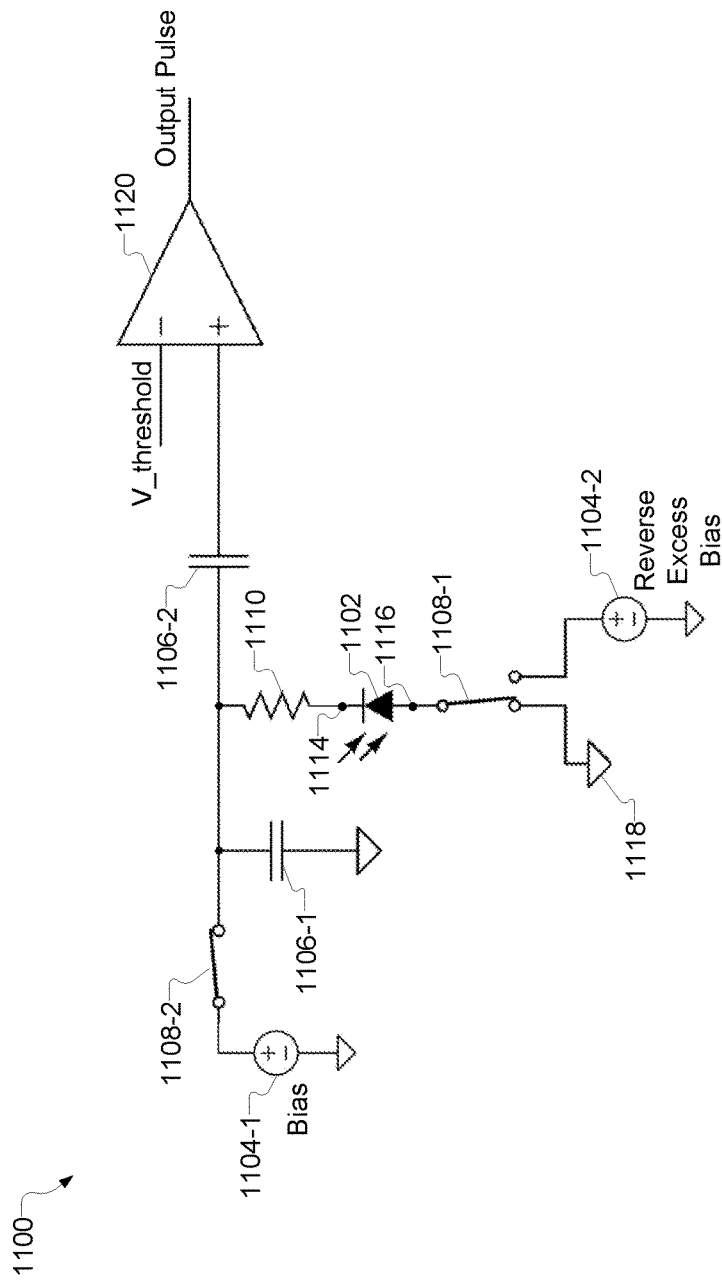
FIG. 11B shows another exemplary SPAD circuit that may be used in the photodetector architectures described herein.

FIG. 11B shows an alternative implementation of SPAD circuit 1100 in which a comparator 1120 is included in SPAD circuit 400 in place of inverter 1112. Comparator 1120 is similar to comparator 420 and is configured to generate an output pulse when a photon hits SPAD 1102 while SPAD 1102 is in the armed state. As shown, a positive terminal of comparator 1120 is connected to output node 1114 of SPAD 1102 by way of capacitor 1106-2. In some examples, capacitor 1106-2 is omitted from SPAD circuit 1100.

When a photon initiates an avalanche within SPAD 1102, SPAD 1102 draws current from capacitor 1106-1, which discharges capacitor 1106-1 to zero. As capacitor 1106-1 is discharged, the voltage at output node 1114 decreases. When the voltage at output node 1114 drops below the threshold voltage on the negative terminal of comparator 1120, comparator 1120 generates an output pulse.

Figure 12:
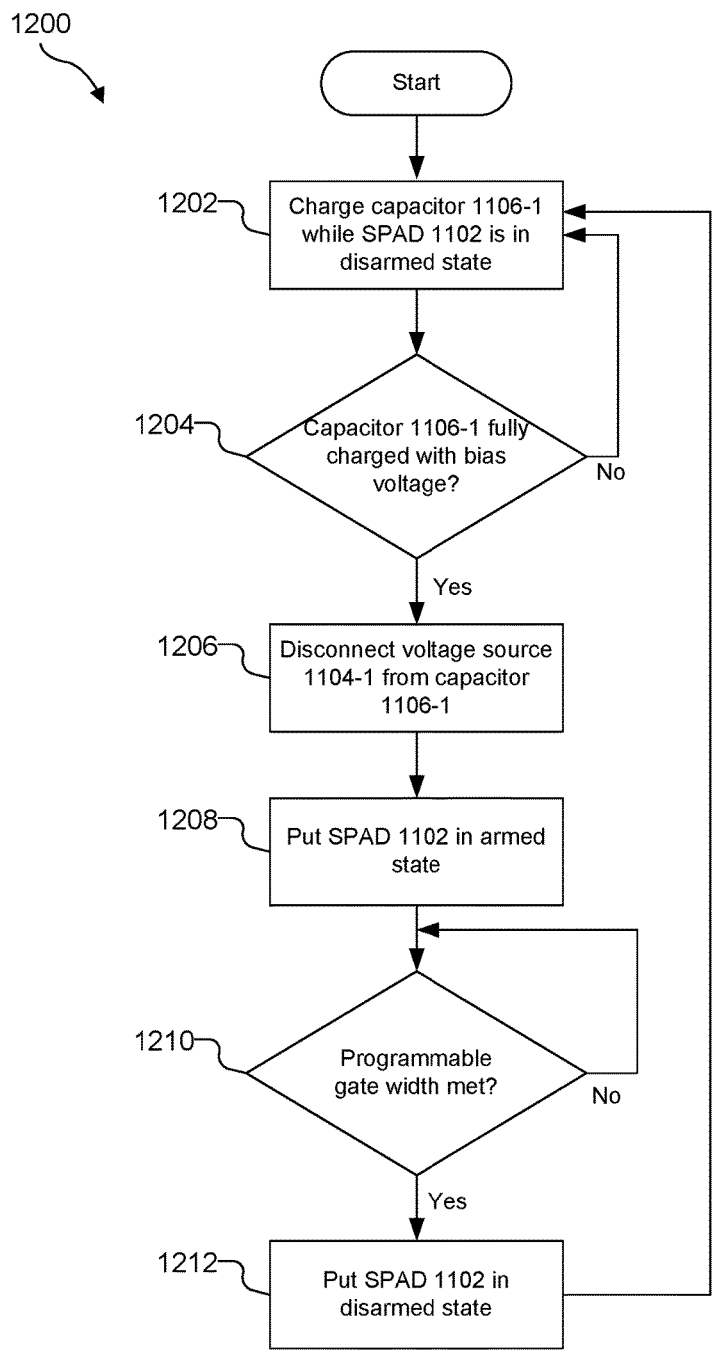
FIG. 12 is a flowchart that illustrates an exemplary mode of operation of the SPAD circuit of FIG. 11A according to principles described herein.

FIG. 12 is a flowchart 1200 that illustrates an exemplary mode of operation of SPAD circuit 1100. For purposes of this example, control circuit 206 is configured to control SPAD circuit 1100 by controlling switches 1108, TDC 208 is connected to the output of inverter 1112, and signal processing circuit 210 is connected to the output of TDC 208. One or more of the operations shown in flowchart 1200 may be performed by control circuit 206.

In operation 1202, capacitor 1106-1 is charged with the bias voltage while SPAD 1102 is in a disarmed state. Control circuit 206 may cause capacitor 1106-1 to be charged with the bias voltage while SPAD 1102 is in the disarmed state by providing control logic that causes switch 1108-1 to be in a first position (i.e., closed) to connect input node 1116 of SPAD 1102 to ground 1118 and switch 1108-2 to be in the first position to connect voltage source 1104-1 to capacitor 1106-1. This switch state is shown in FIG. 11A.

Figure 13:
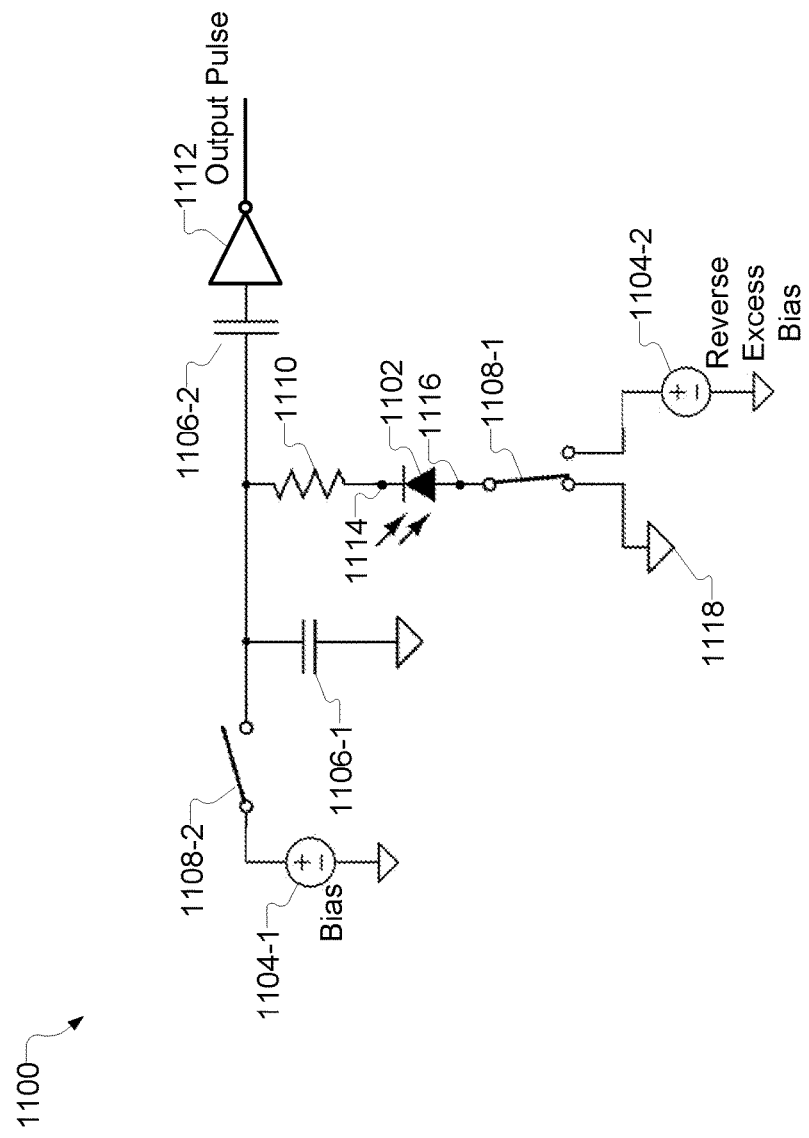
FIGS. 13-14 show exemplary switch states of the SPAD circuit of FIG. 11A.

While in the switch state shown in FIG. 11A, voltage source 1104-1 charges capacitor 1106-1 with the bias voltage. When control circuit 206 detects that capacitor 1106-1 is fully charged with the bias voltage (Yes; decision block 1204), control circuit 1206 disconnects voltage source 1104-1 from capacitor 1106-1 (operation 1206). This is performed by control circuit 1206 providing control logic that causes switch 1108-2 to be in the second position (i.e., open) while switch 1108-1 is still in the first position. This switch state is shown in FIG. 13.

Figure 14:
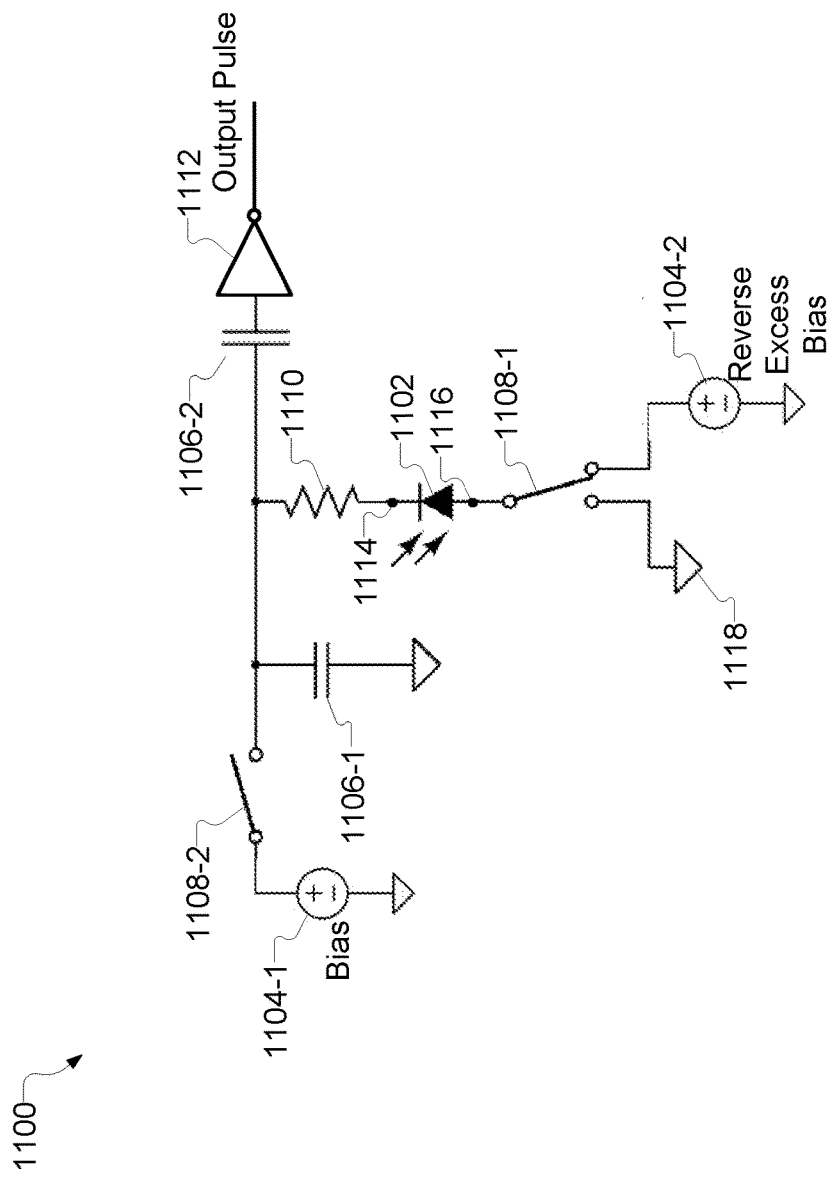
Figure 15:
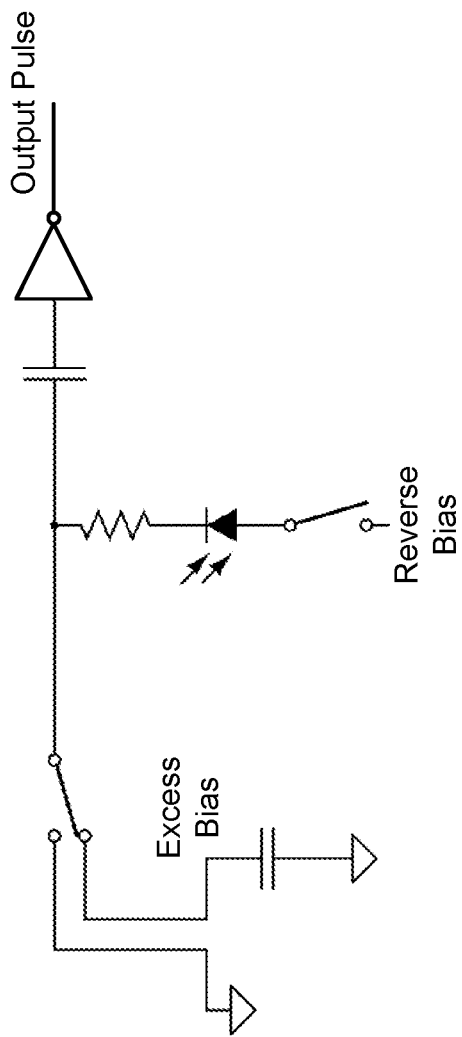
FIGS. 15-20 show alternative circuit topologies of the SPAD circuit of FIG. 11A.
Figure 16:
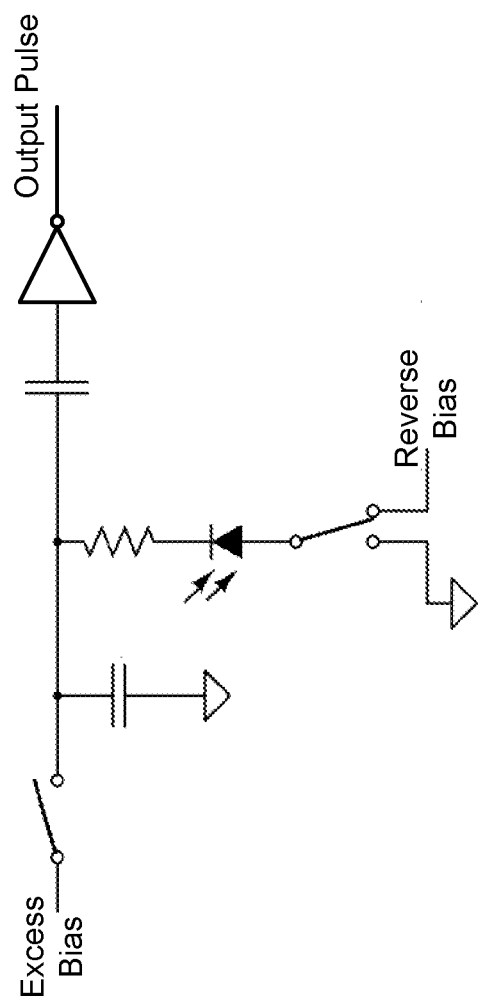
Figure 17:
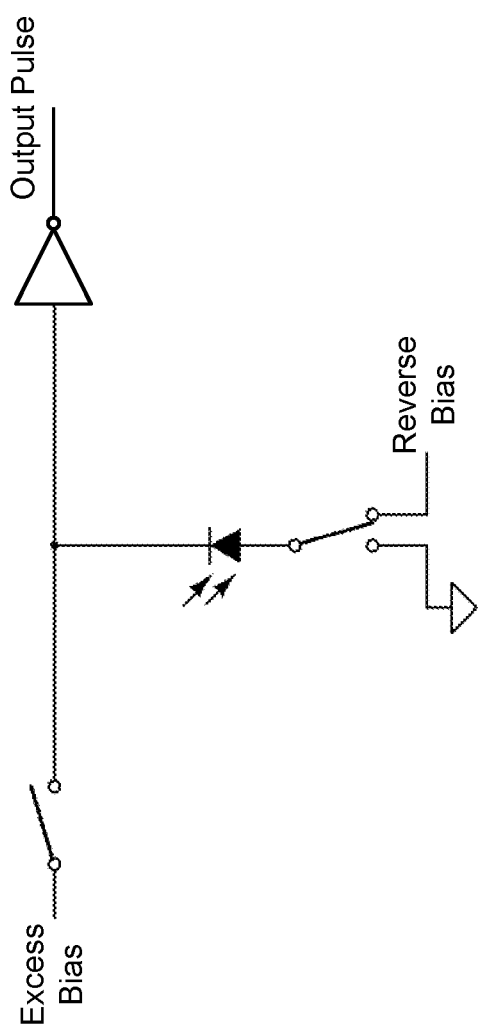
Figure 18:
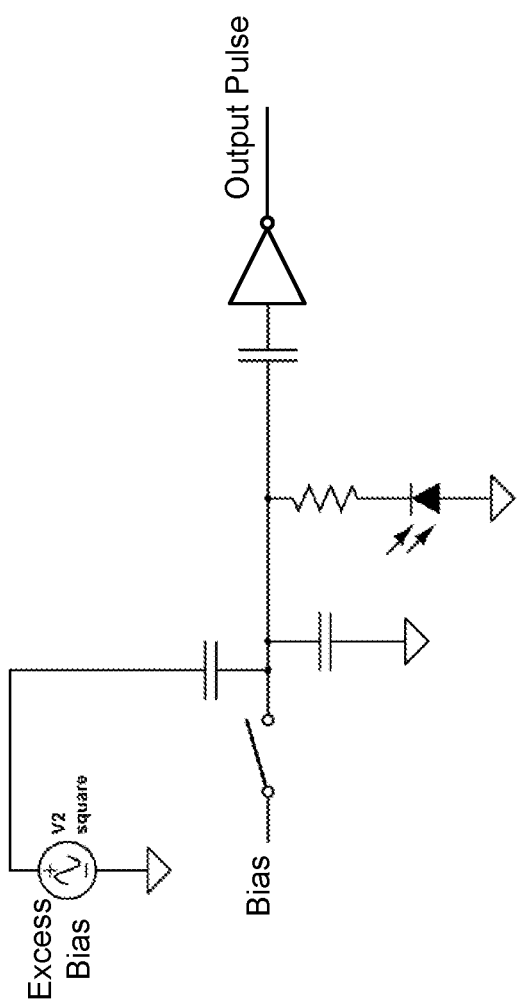
Figure 19:
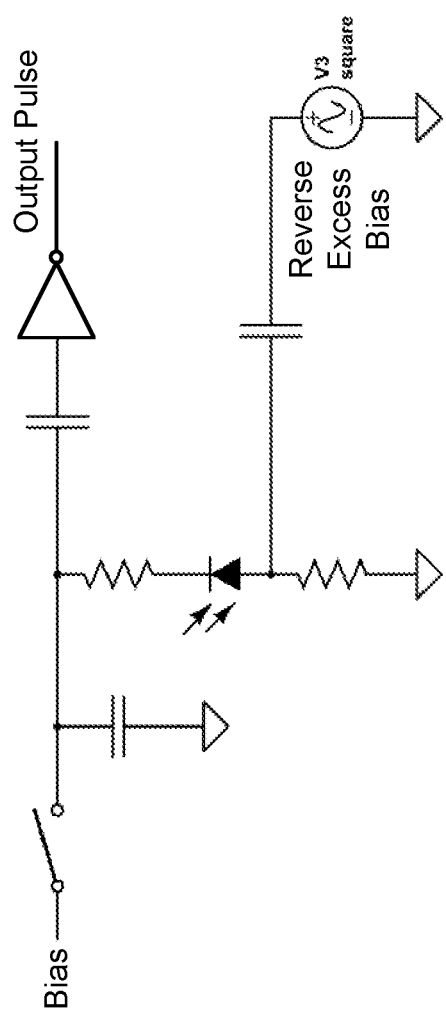
Figure 20:
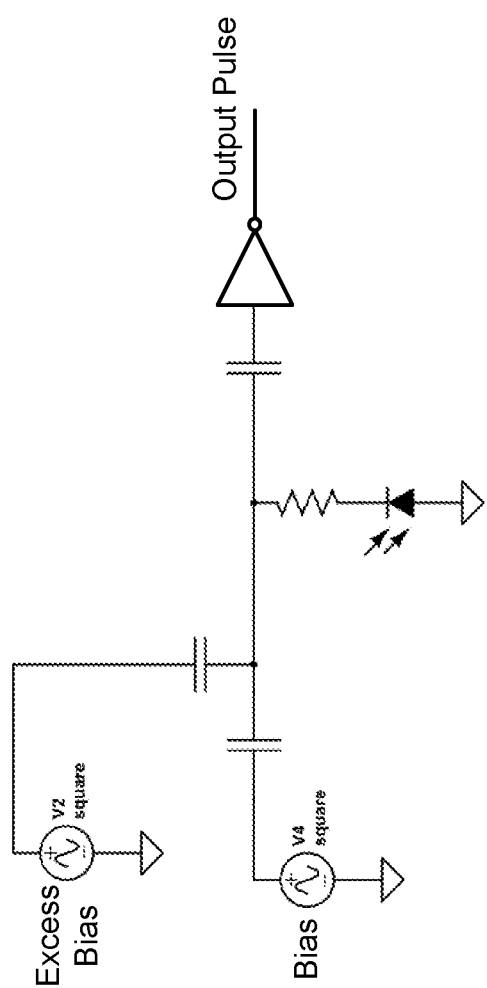

In operation 1208, control circuit 206 puts SPAD 1102 in an armed state while capacitor 1106-1 is charged with the bias voltage. To this end, control circuit 206 provides control logic that causes switch 1108-1 to be in the second position (i.e., open) to connect input node 1116 of SPAD 1102 to voltage source 1104-2. The control logic also keeps switch 1108-2 in the second position to keep voltage source 1104-1 disconnected from capacitor 1106-1. This switch state is shown in FIG. 14. While in the switch state shown in FIG. 14, SPAD 1102 is armed because the voltage across SPAD 1102 is higher than the breakdown voltage of SPAD 1102.

As described above, control circuit 206 may arm and disarm SPAD 1102 in accordance with a programmable gate delay and a programmable gate width. Accordingly, if control circuit 206 detects that the programmable gate width is met (i.e., that the predetermined time specified by the programmable gate width has expired) (Yes; decision block 1210), control circuit 206 puts SPAD 402 back in the disarmed state (operation 1212) by causing switch 1208-1 to be in the first position to connect input node 1116 of SPAD 1102 to ground 1118. The process shown in FIG. 12 may be repeated for subsequent light pulses.

Once SPAD 1102 has been put in the armed state, a photon from the light pulse may initiate an avalanche within SPAD 1102. As described above, SPAD 1102 draws current from capacitor 1106-1 while the avalanche is occurring, which decreases the voltage at output node 1116. When the voltage at output node 1116 drops below a certain value, inverter 1112 generates an output pulse. TDC 208 may process the output pulse as described above.

The various components included in SPAD circuit 1100 may be implemented in any suitable manner. For example, switches 1108 may each be implemented by any suitable switch circuitry, such as the switch circuitry shown in FIGS. 9A-9F. Inverter 1112 may be implemented by the circuitry shown in FIG. 10A. Comparator 1120 may be implemented by the circuitry shown in FIG. 10B.

In some examples, inverter 1112 and comparator 1120 may be omitted from SPAD circuit 1100. In these examples, the output from SPAD 1102 is provided as the input to TDC 208.

SPAD circuit 1110 may be implemented by any of a number of alternative circuit topologies. For example, FIGS. 15-20 show alternative circuit topologies of SPAD circuit 1110. In particular, the circuit topology of FIG. 17 does not include a capacitor that gates the SPAD. Rather, the parasitic capacitance of the SPAD is charged with an excess bias voltage and used to gate the SPAD. This may advantageous in configurations where space limitations limit the number of components that can be included in SPAD circuit 1110.

Figure 21:
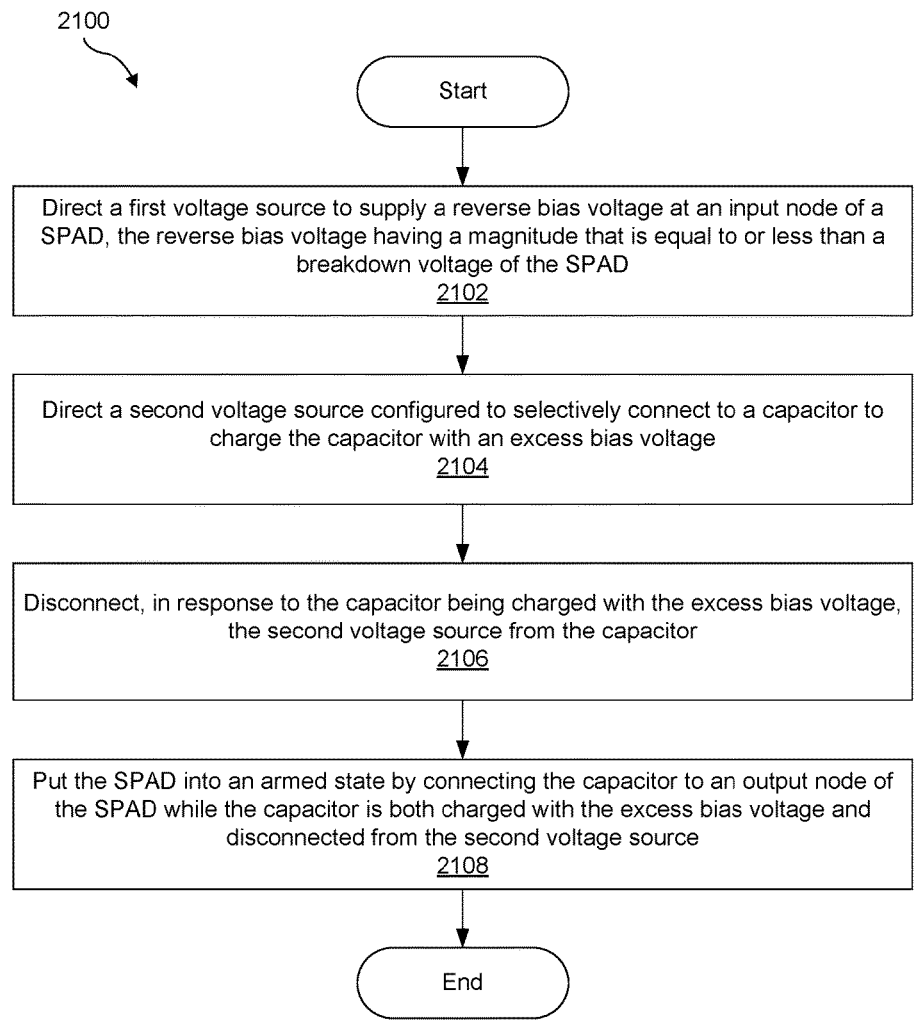
FIG. 21 illustrates an exemplary method according to principles described herein.

FIG. 21 illustrates an exemplary method 2100. While FIG. 21 illustrates exemplary operations according to one embodiment, other embodiments may omit, add to, reorder, and/or modify any of the operations shown in FIG. 21. One or more of the operations shown in FIG. 21 may be performed by control circuit 206 in connection with SPAD circuit 400.

In operation 2102, control circuit 206 directs a first voltage source to supply a reverse bias voltage at an input node of a SPAD, the reverse bias voltage having a magnitude that is equal to or less than a breakdown voltage of the SPAD. Operation 2102 may be performed in any of the ways described herein.

In operation 2104, control circuit 206 directs a second voltage source configured to selectively connect to a capacitor to charge the capacitor with an excess bias voltage. Operation 2104 may be performed in any of the ways described herein.

In operation 2106, control circuit 206 disconnects, in response to the capacitor being charged with the excess bias voltage, the second voltage source from the capacitor. Operation 2106 may be performed in any of the ways described herein.

In operation 2108, control circuit 206 puts the SPAD into an armed state by connecting the capacitor to an output node of the SPAD while the capacitor is both charged with the excess bias voltage and disconnected from the second voltage source. Operation 2108 may be performed in any of the ways described herein.

Figure 22:
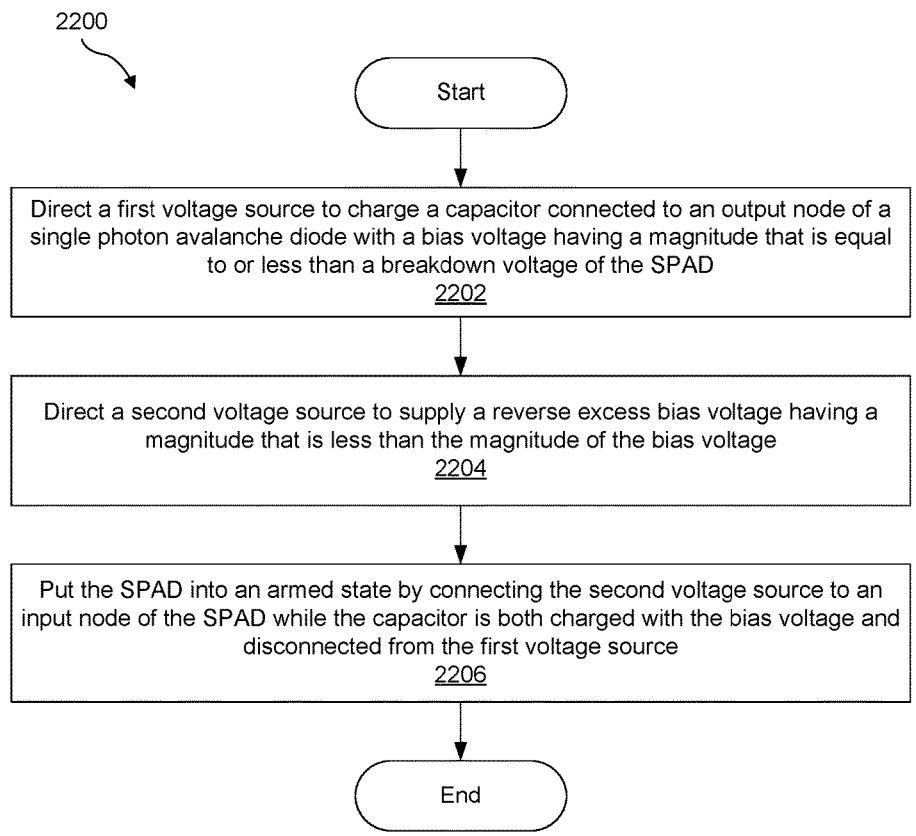
FIG. 22 illustrates another exemplary method according to principles described herein.

FIG. 22 illustrates another exemplary method 2200. While FIG. 22 illustrates exemplary operations according to one embodiment, other embodiments may omit, add to, reorder, and/or modify any of the operations shown in FIG.

22. One or more of the operations shown in FIG. 22 may be performed by control circuit 206 in connection with SPAD circuit 1100.

In operation 2202, control circuit 206 directs a first voltage source to charge a capacitor connected to an output node of a single photon avalanche diode with a bias voltage having a magnitude that is equal to or less than a breakdown voltage of the SPAD. Operation 2202 may be performed in any of the ways described herein.

In operation 2204, control circuit 206 directs a second voltage source to supply a reverse excess bias voltage. Operation 2204 may be performed in any of the ways described herein.

In operation 2206, control circuit 206 puts the SPAD into an armed state by connecting the second voltage source to an input node of the SPAD while the capacitor is both charged with the bias voltage and disconnected from the first voltage source. Operation 2206 may be performed in any of the ways described herein.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A photodetector comprising:
    a single photon avalanche diode (SPAD);
    a first voltage source connected to an input node of the SPAD and configured to supply a reverse bias voltage at the input node, the reverse bias voltage having a magnitude that is equal to or less than a breakdown voltage of the SPAD;
    a capacitor;
    a second voltage source configured to selectively connect to the capacitor to charge the capacitor with an excess bias voltage; and
    a switch configuration configured to put the SPAD into an armed state by connecting the capacitor to an output node of the SPAD while the capacitor is charged with the excess bias voltage and while the capacitor is disconnected from the second voltage source;
    wherein, when the capacitor is connected to the output node of the SPAD, the capacitor supplies the excess bias voltage to the output node of the SPAD such that a voltage across the SPAD is greater than the breakdown voltage.

2. The photodetector of claim 1, wherein the switch configuration is further configured to put the SPAD into a disarmed state by disconnecting the capacitor from the output node of the SPAD and connecting the output node of the SPAD to ground.

3. The photodetector of claim 2, wherein the switch configuration comprises:
    a first switch configured to selectively
        close to connect the output node of the SPAD to the capacitor, and
        open to disconnect the output node of the SPAD from the capacitor; and
    a second switch configured to selectively
        close to connect the output node of the SPAD to ground, and
        open to disconnect the output node of the SPAD from ground.

4. The photodetector of claim 3, wherein the switch configuration further comprises:
    a third switch configured to selectively
        close to connect the second voltage source to the capacitor to charge the capacitor with the excess bias voltage, and
        open to disconnect the second voltage source from the capacitor in response to the capacitor being charged with the excess bias voltage.

5. The photodetector of claim 4, further comprising a control circuit configured to control the switch configuration, wherein the control circuit is configured to cause the capacitor to be charged with the excess bias voltage while the SPAD is in the disarmed state by:
    opening the first switch to disconnect the output node of the SPAD from the capacitor;
    closing the second switch to connect the output node of the SPAD to ground; and
    closing the third switch to connect the second voltage source to the capacitor.

6. The photodetector of claim 5, wherein the control circuit is further configured to open the third switch, while the first switch is still open and the second switch is still closed, to disconnect the second voltage source from the capacitor in response to the capacitor being charged with the excess bias voltage.

7. The photodetector of claim 6, wherein the control circuit is further configured to put the SPAD in the armed state while the capacitor is charged with the excess bias voltage by:
    closing the first switch to connect the output node of the SPAD to the capacitor;
    opening the second switch to disconnect the output node of the SPAD from ground; and
    keeping the third switch open to keep the second voltage source disconnected from the capacitor.

8. The photodetector of claim 7, wherein the control circuit is further configured to:
    maintain data representative of a programmable gate delay;
    detect an occurrence of a light pulse while the SPAD is in the disarmed state; and
    put the SPAD in the armed state a predetermined amount of time, as specified by the programmable gate delay, after the occurrence of the light pulse.

9. The photodetector of claim 8, wherein the control circuit is further configured to:
    maintain data representative of a programmable gate width; and
    put the SPAD in the disarmed state a predetermined amount of time, as specified by the programmable gate width, after the SPAD is put into the armed state by
        opening the first switch to disconnect the output node of the SPAD from the capacitor, and
        closing the second switch to connect the output node of the SPAD to ground.

10. The photodetector of claim 8, further comprising an inverter connected to the output node of the SPAD, wherein the inverter generates an output pulse when a voltage on the output node drops below a certain value in response to an avalanche occurring within the SPAD, the avalanche occurring in response to a photon from the light pulse hitting the SPAD while the SPAD is in the armed state.

11. The photodetector of claim 10, further comprising:

a time-to-digital converter connected to an output of the inverter and configured to output data representative of a time difference between an occurrence of the output pulse and the occurrence of the light pulse; and a signal processing circuit connected to an output of the time-to-digital converter and configured to perform an operation on the data output by the time-to-digital converter.

12. The photodetector of claim 1, further comprising a resistor that has a first node connected to the output node of the SPAD and a second node, wherein the switch configuration connects the capacitor to the output node of the SPAD by connecting the capacitor to the second node of the resistor.

13. A method comprising:

directing a first voltage source to supply a reverse bias voltage at an input node of a single photon avalanche diode (SPAD), the reverse bias voltage having a magnitude that is equal to or less than a breakdown voltage of the SPAD;

directing a second voltage source configured to selectively connect to a capacitor to charge the capacitor with an excess bias voltage, the excess bias voltage having a magnitude that is less than the magnitude of the reverse bias voltage supplied by the first voltage source;

disconnecting, in response to the capacitor being charged with the excess bias voltage, the second voltage source from the capacitor; and putting the SPAD into an armed state by connecting the capacitor to an output node of the SPAD while the capacitor is both charged with the excess bias voltage and disconnected from the second voltage source;

wherein, when the capacitor is connected to the output node of the SPAD, the capacitor supplies the excess bias voltage to the output node of the SPAD such that a voltage across the SPAD is greater than the breakdown voltage.

14. The method of claim 13, further comprising putting the SPAD into a disarmed state by disconnecting the capacitor from the output node of the SPAD and connecting the output node of the SPAD to ground.

15. The method of claim 14, wherein a first switch is configured to selectively
close to connect the output node of the SPAD to the capacitor, and
open to disconnect the output node of the SPAD from the capacitor;

a second switch is configured to selectively
close to connect the output node of the SPAD to ground, and
open to disconnect the output node of the SPAD from ground; and a third switch configured to selectively
close to connect the second voltage source to the capacitor to charge the capacitor with the excess bias voltage, and
open to disconnect the second voltage source from the capacitor in response to the capacitor being charged with the excess bias voltage.

16. The method of claim 15, further comprising causing the capacitor to be charged with the excess bias voltage while the SPAD is in the disarmed state by:

opening the first switch to disconnect the output node of the SPAD from the capacitor;

closing the second switch to connect the output node of the SPAD to ground; and closing the third switch to connect the second voltage source to the capacitor.

17. The method of claim 16, further comprising opening the third switch, while the first switch is still open and the second switch is still closed, to disconnect the second voltage source from the capacitor in response to the capacitor being charged with the excess bias voltage.

18. The method of claim 17, further comprising putting the SPAD in the armed state while the capacitor is charged with the excess bias voltage by:

closing the first switch to connect the output node of the SPAD to the capacitor;

opening the second switch to disconnect the output node of the SPAD from ground; and keeping the third switch open to keep the second voltage source disconnected from the capacitor.

19. The method of claim 18, further comprising:

maintaining data representative of a programmable gate delay;

detecting an occurrence of a light pulse while the SPAD is in the disarmed state; and putting the SPAD in the armed state a predetermined amount of time, as specified by the programmable gate delay, after the occurrence of the light pulse.

20. The method of claim 19, further comprising:

maintaining data representative of a programmable gate width; and putting the SPAD in the disarmed state a predetermined amount of time, as specified by the programmable gate width, after the SPAD is put into the armed state by
opening the first switch to disconnect the output node of the SPAD from the capacitor, and
closing the second switch to connect the output node of the SPAD to ground.

21. A photodetector comprising:

a single photon avalanche diode (SPAD);

a capacitor connected to an output node of the SPAD;

a first voltage source configured to selectively connect to the capacitor to charge the capacitor with a bias voltage having a magnitude that is equal to or less than a breakdown voltage of the SPAD;

a second voltage source configured to supply a reverse excess bias voltage having a magnitude that is less than the magnitude of the bias voltage; and a switch configuration configured to put the SPAD into an armed state by connecting the second voltage source to an input node of the SPAD while the capacitor is both charged with the bias voltage and disconnected from the first voltage source.

22. The photodetector of claim 21, wherein the switch configuration is further configured to put the SPAD into a disarmed state by disconnecting the second voltage source from the input node of the SPAD and connecting the input node of the SPAD to ground.

23. The photodetector of claim 22, wherein the switch configuration comprises a first switch configured to selectively be in a first position to connect the input node of the SPAD to ground; and be in a second position to connect the input node of the SPAD to the second voltage source.

24. The photodetector of claim 23, wherein the switch configuration further comprises a second switch configured to selectively be in a first position to connect the first voltage source to the capacitor; and be in a second position to disconnect the first voltage source from the capacitor.

25. The photodetector of claim 24, further comprising a control circuit configured to control the switch configuration, wherein the control circuit is configured to cause the capacitor to be charged with the bias voltage while the SPAD is in the disarmed state by:
   causing the first switch to be in the first position to connect the input node of the SPAD to ground; and
   causing the second switch to be in the first position to connect the first voltage source to the capacitor.

26. The photodetector of claim 25, wherein the control circuit is further configured to cause the second switch to be in the second position, while the first switch is still in the first position, to disconnect the first voltage source from the capacitor in response to the capacitor being charged with the bias voltage.

27. The photodetector of claim 26, wherein the control circuit is further configured to put the SPAD in the armed state while the capacitor is charged with the bias voltage by:
   causing the first switch to be in the second position to connect the input node of the SPAD to the second voltage source; and
   keeping the second switch in the second position to keep the first voltage source disconnected from the capacitor.

28. The photodetector of claim 27, wherein the control circuit is further configured to:
   maintain data representative of a programmable gate delay;
   detect an occurrence of a light pulse while the SPAD is in the disarmed state; and
   put the SPAD in the armed state a predetermined amount of time, as specified by the programmable gate delay, after the occurrence of the light pulse.

29. The photodetector of claim 28, wherein the control circuit is further configured to:
   maintain data representative of a programmable gate width; and
   put the SPAD in the disarmed state a predetermined amount of time, as specified by the programmable gate width, after the SPAD is put into the armed state by causing the first switch to be in the first position to connect the input node of the SPAD to ground.

30. The photodetector of claim 28, further comprising an inverter connected to the output node of the SPAD, wherein the inverter generates an output pulse when a voltage on the output node drops below a certain value in response to an avalanche occurring within the SPAD, the avalanche occurring in response to a photon from the light pulse hitting the SPAD while the SPAD is in the armed state.

* * * * *